United States Patent [19]

Hagiwara

[11] Patent Number: 5,736,735
[45] Date of Patent: Apr. 7, 1998

[54] OPTICAL SCANNING DEVICE AND FOREIGN MATTER INSPECTION APPARATUS

[75] Inventor: Tsuneyuki Hagiwara, Tokyo, Japan

[73] Assignee: Nikon Corporation, Tokyo, Japan

[21] Appl. No.: 715,638

[22] Filed: Sep. 18, 1996

[30] Foreign Application Priority Data

Sep. 21, 1995 [JP] Japan ................................ 7-267741
Nov. 10, 1995 [JP] Japan ................................ 7-317130

[51] Int. Cl.$^6$ .................................................. G02F 1/01
[52] U.S. Cl. .................... 250/225; 250/559.4; 250/234; 359/281
[58] Field of Search .................................. 250/225, 234, 250/559.4, 235; 356/364, 368, 240, 241, 430; 359/281, 283, 298, 301, 198

[56] References Cited

U.S. PATENT DOCUMENTS 4,943,734  7/1990  Johnson et al. ........................ 250/572
5,436,464  7/1995  Hayano et al. ........................ 250/225

Primary Examiner—Que Le
Attorney, Agent, or Firm—Shapiro and Shapiro

[57] ABSTRACT

An optical scanning device includes a light deflection unit for deflecting a light beam emitted by a light source to be incident on an object to be irradiated, a polarization state adjusting unit for adjusting the polarization state of the light beam, so that the light beam to be incident on the object to be irradiated has a predetermined polarization state with respect to the object to be irradiated, and a rotary driving unit for rotating the light deflection unit and the polarization state adjusting unit together so that the light beam deflected by the light deflection unit scans the object to be irradiated.

15 Claims, 15 Drawing Sheets

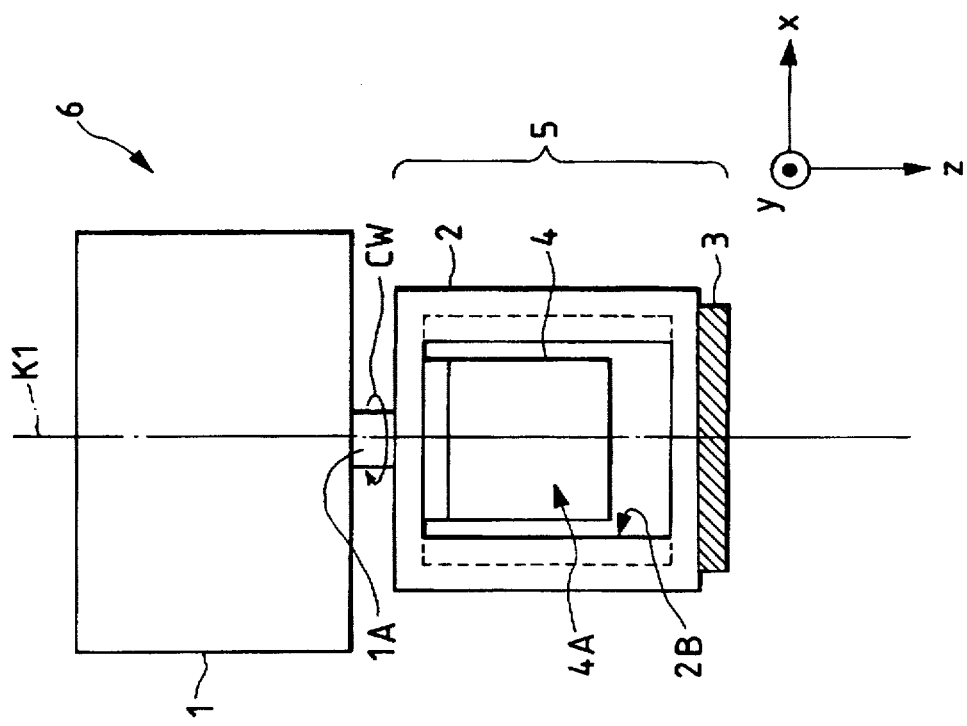
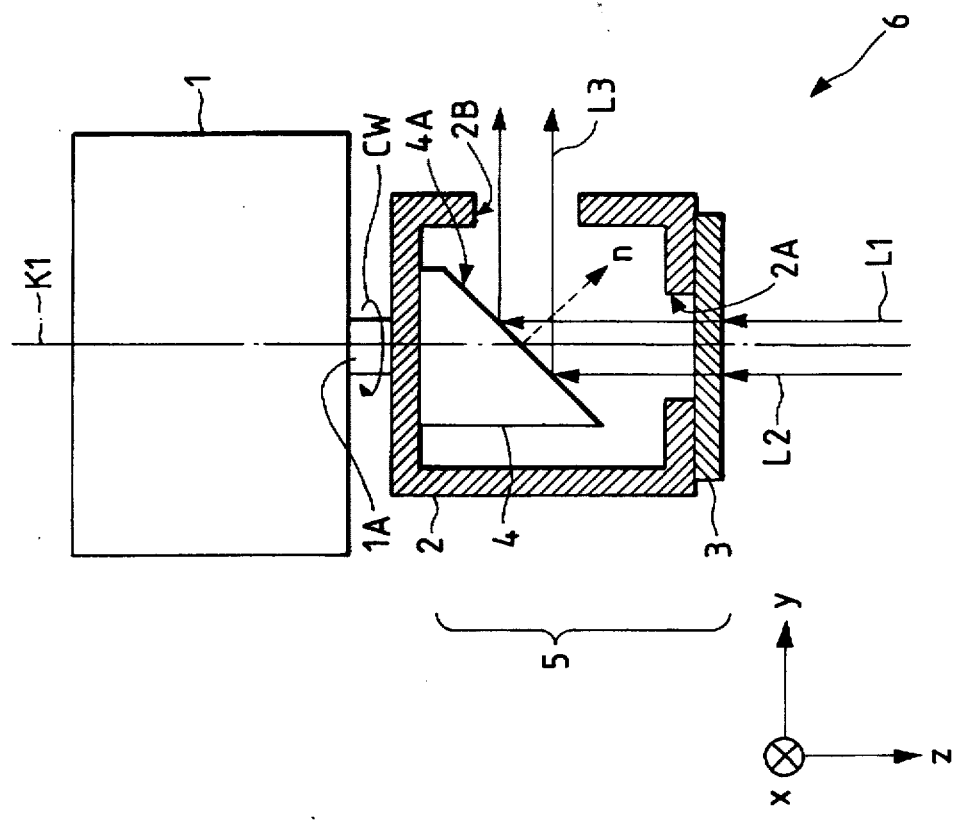

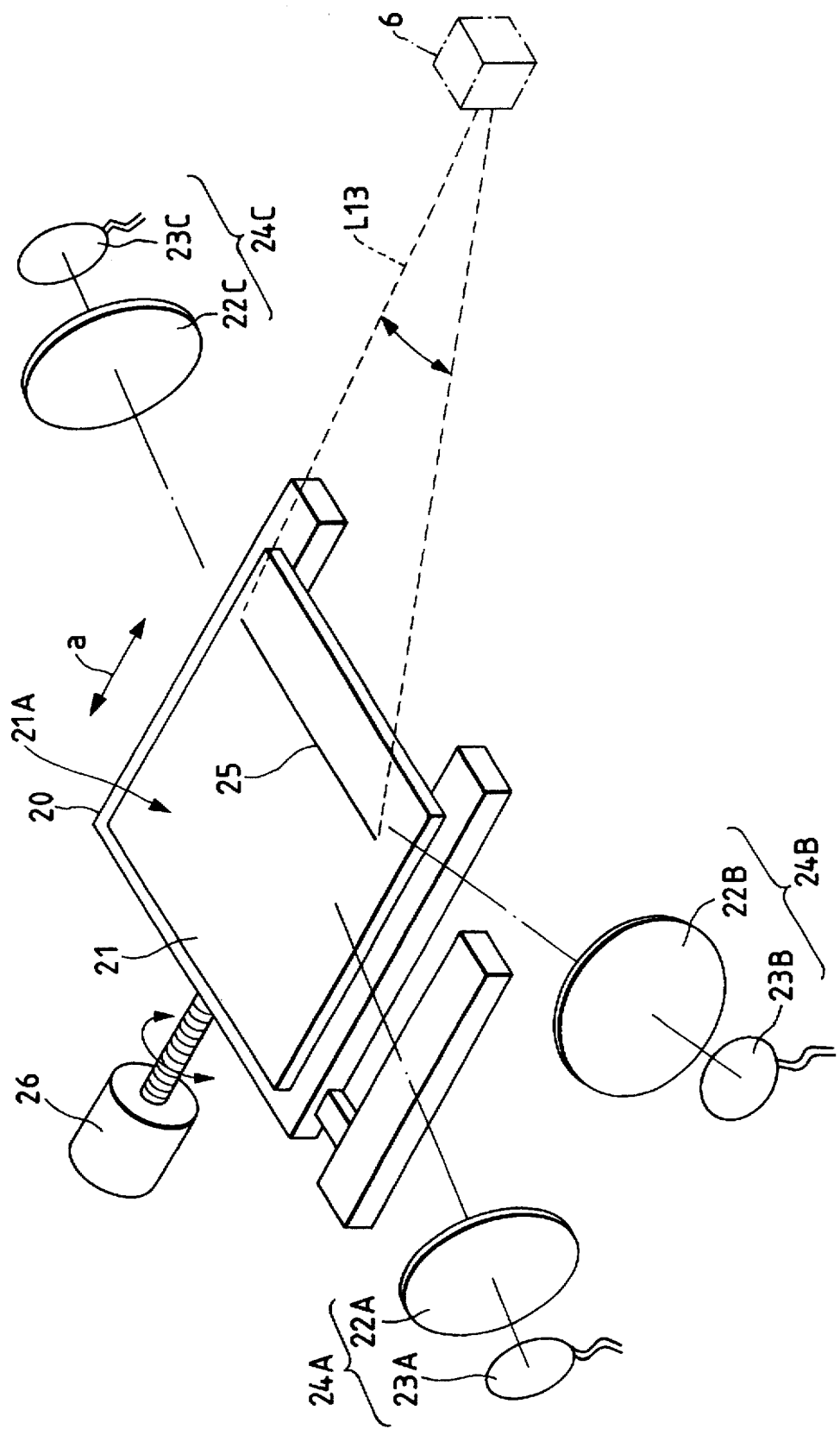

OPTICAL SCANNING DEVICE AND FOREIGN MATTER INSPECTION APPARATUS

BACKGROUND OF THE INVENTION

1. Field of the Invention

The present invention relates to an optical scanning device and a foreign matter inspection apparatus and, for example, to a device which is suitably applied for a foreign matter inspection apparatus for inspecting the presence/absence of foreign matter or the like on the surface of a large-scale substrate such as a liquid crystal manufacturing mask or the like.

2. Related Background Art

In a conventional foreign matter inspection apparatus, a focused light beam is scanned on the surface to be inspected of a substrate to be inspected, and scattered light generated by foreign matter attached to the surface to be inspected is received by a plurality of light-receiving elements arranged around the substrate. Based on the outputs from these light-receiving elements, the presence/absence of foreign matter or the like on the surface to be inspected of the substrate to be inspected can be detected.

In this case, such foreign matter inspection apparatus popularly adopts, as a method of scanning a focused light beam on the surface to be inspected of the substrate to be inspected, a method of deflecting a light beam emitted by a laser beam source toward the surface to be inspected of the substrate to be inspected using a scanner such as a galvano mirror, polygonal mirror, or the like, and focusing the deflected light beam onto the surface to be inspected of the substrate to be inspected via a focusing lens such as an f-θ lens, fsin$^{-1}$-θ lens, or the like.

However, when the optical system of the foreign matter inspection apparatus is arranged, as described above, if a large-scale substrate is to be inspected, a focusing lens with a large field angle is required. However, it is very difficult to design and manufacture a large-field angle focusing lens with optically small aberrations.

The foreign matter inspection apparatus with the above arrangement uses a galvano mirror or a polygonal mirror in the method of scanning the focused light beam onto the surface to be inspected of the substrate to be inspected. However, since the upper limit scan frequency of the galvano mirror is determined by reciprocal motions, the inspection speed is limited. On the other hand, it is very difficult for the polygonal mirror to attain tilting correction between surfaces. Hence, it is difficult to achieve ideal optical performance.

SUMMARY OF THE INVENTION

The present invention has been made in consideration of the above situation, and has as its object to provide an optical scanning device and a foreign matter inspection apparatus, which can scan a large area at high speed.

For example, a glass substrate has a higher reflectance for s-polarized light waves than that for p-polarized light waves. On the other hand, in a substrate formed with a pattern consisting of a metal material, p-polarized light waves are known to generate scattered light at a pattern edge more easily than s-polarized light waves.

Therefore, in the above-mentioned foreign matter inspection apparatus, high-precision foreign matter inspection can be attained when the surface to be inspected of a substrate to be inspected is always scanned with a light beam consisting of s-polarized light waves.

Therefore, if an optical system which can scan a large area with a light beam which is always in a predetermined polarization state with respect to the plane of incidence at high speed can be constituted, a foreign matter inspection apparatus which has higher inspection efficiency and precision than those of a conventional one can be realized.

The present invention has been made in consideration of the above situation, and has as its object to provide an optical scanning device and a foreign matter inspection apparatus, which can scan a large area with a light beam which is always in a predetermined polarization state at high speed.

In order to achieve the above objects, according to the first aspect of the present invention, there is provided an optical scanning device comprising light deflection means for deflecting a light beam emitted by a light source to be incident on an object to be irradiated, polarization state adjusting means for adjusting a polarization state of the light beam, so that the light beam to be incident on the object to be irradiated has a predetermined polarization state with respect to the object to be irradiated, and rotary driving means for rotating the light deflection means and the polarization state adjusting means together so that the light beam deflected by the light deflection means scans the object to be irradiated.

According to the second aspect of the present invention, there is provided a foreign matter inspection apparatus for inspecting a presence/absence of foreign matter attached to a surface to be inspected of an object to be inspected, and the foreign matter inspection apparatus comprises a light source for emitting a light beam, light deflection means for deflecting the light beam emitted by the light source to be incident on the surface to be inspected of the object to be inspected, polarization state adjusting means for adjusting a polarization state of the light beam, so that the light beam to be incident on the surface to be inspected of the object to be inspected has a predetermined polarization state with respect to the surface to be inspected of the object to be inspected, rotary driving means for rotating the light deflection means and the polarization state adjusting means together so that the light beam deflected by the light deflection means scans the surface to be inspected of the object to be inspected, light-receiving means for receiving scattered light of the light beam generated by the foreign matter attached to the surface to be inspected of the object to be inspected, and outputting an electrical signal corresponding to an intensity of the received scattered light, and signal processing means for detecting the foreign matter on the basis of the electrical signal supplied from the light-receiving means.

According to the third aspect of the present invention, there is provided an optical scanning device comprising rotary driving means having a rotation axis, and light deflection means for wavefront-splitting an incident light beam incident along a first optical axis parallel to the rotation axis into a first light beam that forms a first angle with respect to the first optical axis and a second light beam that forms a second angle with respect to the first optical axis, deflecting the first and second light beams in a rotation direction of the rotation axis with reference to a central position of the wavefront-splitting to cause the first and second light beams to be incident on an object to be irradiated, and compensating for a surface run-out error caused by a change in one or both the first and second angles on the basis of a relative angular deviation between the rotation axis and the first optical axis so as to maintain the first and second angles to be a constant value, wherein the rotary driving means integrally rotates the light deflection means about the rotation axis, so that the first and second light beams wavefront-split and deflected by the light deflection means scan the object to be irradiated.

Furthermore, according to the fourth aspect of the present invention, there is provided a foreign matter inspection apparatus for inspecting a presence/absence of foreign matter attached to a surface to be inspected of an object to be inspected, and the foreign matter inspection apparatus comprises a light source for emitting a light beam, rotary driving means having a rotation axis, light deflection means, arranged on an optical path, of the light beam, for wavefront-splitting an incident light beam incident along a first optical axis parallel to the rotation axis into a first light beam that forms a first angle with respect to the first optical axis and a second light beam that forms a second angle with respect to the first optical axis, deflecting the first and second light beams in a rotation direction of the rotation axis with reference to a central position of the wavefront-splitting to cause the first and second light beams to be incident on a surface to be inspected of the object to be inspected, and compensating for a surface run-out error caused by a change in one or both the first and second angles on the basis of a relative angular deviation between the rotation axis and the first optical axis so as to maintain the first and second angles to be a constant value, light-receiving means for receiving scattered light of the first and second light beams generated by the foreign matter attached to the surface to be inspected of the object to be inspected, and outputting an electrical signal corresponding to an intensity of the received scattered light, and signal processing means for detecting the foreign matter on the basis of the electrical signal supplied from the light-receiving means, wherein the rotary driving means integrally rotates the light deflection means about the rotation axis, so that the first and second light beams wavefront-split and deflected by the light deflection means scan the surface to be inspected of the object to be inspected.

Preferably, the optical scanning device comprises polarization state adjusting means for adjusting a polarization state of the incident light beam so that the incident light beam deflected by the light deflection means has a predetermined deflection state with respect to the object to be irradiated (object to be scanned, and the rotary driving means rotates the light deflection means and the polarization state adjusting means together about the rotation axis, so that the first and second light beams wavefront-split and deflected by the light deflection means scan the object to be irradiated (object to be scanned).

In the third and fourth aspects of the present invention, the optical scanning device comprises the light deflection means for wavefront-splitting an incident light beam incident along the first optical axis parallel to the rotation axis into a first light beam, which forms a first angle with the first optical axis, and a second light beam which forms a second angle with the first optical axis, deflecting the first and second light beams in the rotational direction of the rotation axis with reference to the central position of wavefront splitting to become incident on an object to be irradiated, and maintaining the first and second angles to be constant values by compensating for a surface run-out error, generated due to a change in one or both of the first and second angles, on the basis of a relative angular deviation between the rotation axis and the first optical axis. Hence, even when the rotation axis of the rotation driving means suffers a static or dynamic axial run-out, the first and second light beams can be physically stably scanned on the object to be irradiated (object to be inspected) without being influenced by the axial run-out. Furthermore, the optical scanning device comprises the polarization state adjusting means for adjusting the polarization state of an incident light beam, so that the incident light beam deflected by the light deflection means has a predetermined polarization state with respect to the object to be irradiated (object to be inspected). Hence, even a large object to be irradiated (object to be inspected) can be coped with, and foreign matter can be detected with high precision.

The above and other objects, features and advantages of the present invention will be explained hereinafter and may be better understood by reference to the drawings and the descriptive matter which follows.

BRIEF DESCRIPTION OF THE DRAWINGS

FIGS. 1A and 1B are respectively a front view and a side view showing the arrangement of an optical scanning device to be applied to a foreign matter inspection apparatus according to the first embodiment of the present invention;

FIG. 4 is a schematic perspective view showing the arrangement of the foreign matter inspection apparatus shown in FIG. 3;

DETAILED DESCRIPTION OF THE PREFERRED EMBODIMENTS (1) First Embodiment (1-1) Principle A case will be examined below wherein a right-circularly polarized light beam L1 is to be incident, along a rotation axis K1 parallel to the z-direction, on an optical scanning device 6 in which an optical unit 5 constituted by a housing 2, a quarter-wave plate 3, and a reflection mirror 4 is fixed to a drive shaft 1A of a motor 1, as shown in FIGS. 1A and 1B. FIG. 1A is a front view of the optical scanning device 6, and FIG. 1B is a side view thereof.

Figure 2:
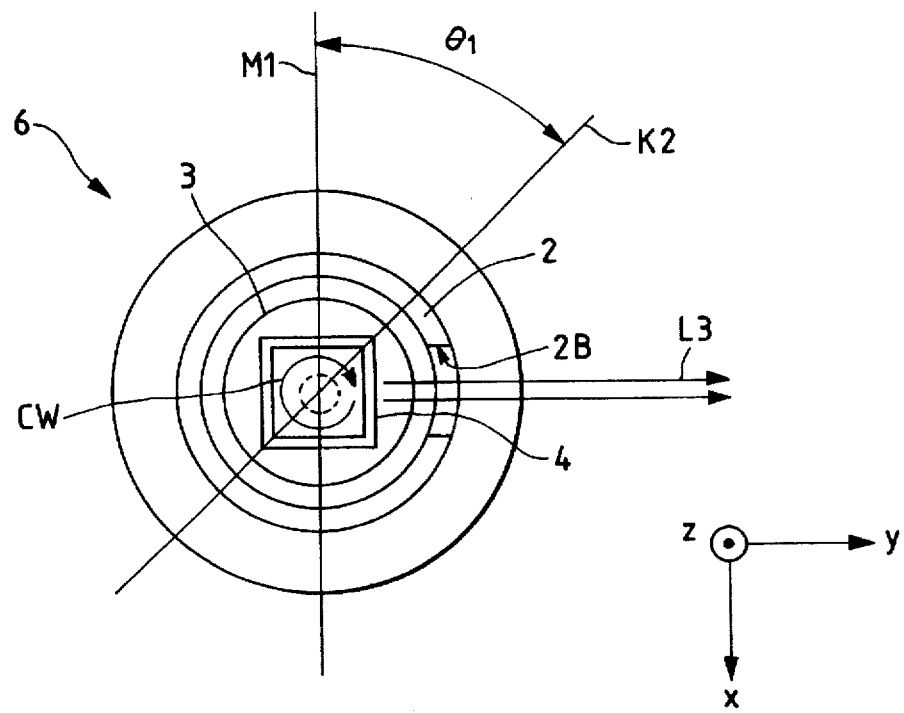
FIG. 2 is a perspective view showing a state wherein the optical scanning device shown in FIGS. 1A and 1B is viewed from the above.

In this case, assume that the motor 1 rotates, via the drive shaft 1A, the optical unit 5 in a direction indicated by an arrow CW about the rotation axis K1. Also, in the optical unit 5, the quarter-wave plate 3 is fixed to the lower surface of the housing 2 to cover a window 2A formed on the bottom surface of the housing 2, and the reflection mirror 4 is fixed inside the housing 2 so that its reflection surface 4A tilted at 45° with respect to the rotation axis K1 opposes a window 2B formed on the circumferential side surface of the housing 2.

At this time, a light beam L1 entering the optical unit 5 of the optical scanning device 6 is phase-modulated by the quarter-wave plate 3 to be converted into a linearly polarized light beam L2, and the light beam L2 is incident on the reflection surface 4A of the reflection mirror 4 via the window 2A of the housing 2. The light beam L2 is reflected by the reflection surface 4A, and exits, as a light beam L3, the optical unit 5 via the window 2B of the housing 2.

In this case, in FIG. 1A, since both a normal n to the reflection surface 4A of the reflection mirror 4 (this normal will be simply referred to as a normal n hereinafter) and the light beam L2 incident on the reflection surface 4A are present in the y-z plane, the light beam L3 emerging from the reflection surface 4A of the reflection mirror 4 is also present in the y-z plane. At this time, the normal n rotates about the rotation axis K1 in synchronism with the rotation of the optical unit 5. Since the plane of incidence of the light beam L2 with respect to the reflection surface 4A of the reflection mirror 4 agrees with the z-n plane, the light beam L3 is always present in the z-n plane owing to the law of reflection.

Therefore, the light beam L1 entering the optical scanning device 6 exits the optical unit 5 while being deflected in a direction that always makes an angle of 45° with the normal n, so that its exit direction rotates about the rotation axis K1 to follow the rotation of the optical unit 5.

As shown in the upper perspective view of the optical scanning device 6 shown in FIG. 2, the quarter-wave plate 3 is arranged in this optical scanning device 6, so that an optic axis K2 of the quarter-wave plate 3 is tilted at $\theta_1$ (=45°) with respect to a straight line M1 parallel to the reflection surface 4A of the reflection mirror 4 and perpendicular to the rotation axis K1 in a plane including the straight line M1 and perpendicular to the rotation axis K1.

In this case, since the light beam L1 entering the optical unit 5 is phase-modulated by the quarter-wave plate 3, it is converted into a linearly polarized light beam L2 (FIG. 1A), the plane of vibration of an electric vector of which is always perpendicular to the z-n plane (FIG. 1A). Thereafter, the light beam L2 is deflected by the reflection mirror 4 in the direction perpendicular to the rotation axis K1 (FIG. 1A).

Therefore, in this optical scanning device 6, since the direction of vibration of the electric vector of the light beam L3 emerging from the reflection mirror 4 is always perpendicular to the z-n plane (FIG. 1A) irrespective of the rotation angle of the optical unit 5, the surface to be irradiated of an object to be irradiated disposed around the optical unit 5 to shield the optical path of the light beam L3 can be scanned with the light beam L3 which is always in a roughly constant polarization state.

When the direction of rotation of the circularly polarized light beam L1 incident on the reflection mirror 4 is reversed, the plane of polarization of the linearly polarized light beam L3 emerging from the mirror 4 rotates 90°, and the direction of vibration of its electric vector becomes parallel to the z-n plane, needless to say.

Figure 3:
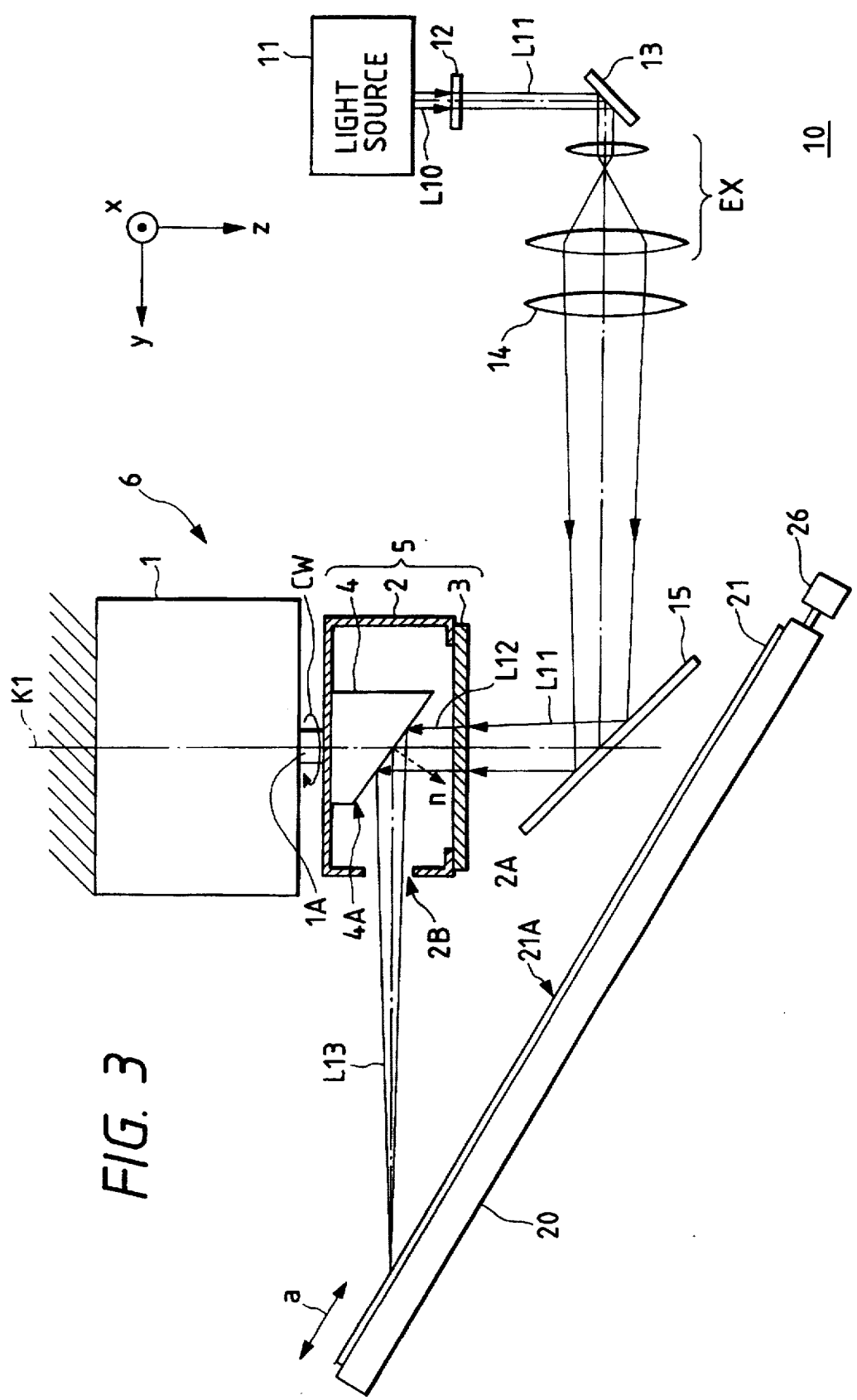
FIG. 3 is a side view showing the arrangement of the foreign matter inspection apparatus according to the first embodiment of the present invention.

(1-2) Arrangement of Foreign Matter Inspection Apparatus According to First Embodiment Referring to FIG. 3 in which the same reference numerals denote corresponding portions in FIGS. 1A and 1B, reference numeral 10 indicates a foreign matter inspection apparatus according to the first embodiment as a whole. In this apparatus, a right-circularly polarized light beam L11 is formed by phase-modulating a linearly-polarized light beam L10 emitted by a laser beam source 11 by a quarter-wave plate 12.

This light beam L11 is incident on a beam expander lens system EX via a reflection mirror 13, and is expanded by the beam expander lens system EX. Thereafter, the light beam L11 enters the optical scanning device 6 along the axis K1 via a lens 14 and a reflection mirror 15 in turn.

At this time, as shown in FIG. 2, the quarter-wave plate 3 is arranged in this optical scanning device 6, so that the optic axis K2 of the quarter-wave plate 3 is tilted at $\theta_1$ (=45°) with respect to the straight line M1 parallel to the reflection surface 4A of the reflection mirror 4 and perpendicular to the rotation axis K1 in the plane including the straight line M1 and perpendicular to the rotation axis K1.

In this fashion, the light beam L11 entering the optical scanning device 6 is phase-modulated by the quarter-wave plate 3 in the optical unit 5 to a linearly polarized light beam L12, the plane of vibration of the electric vector of which is always perpendicular to the z-n plane. Thereafter, the light beam L12 is reflected by the reflection surface 4A of the reflection mirror 4, and exits the optical scanning device 6 as a light beam L13, the plane of vibration of the electric vector of which is always perpendicular to the z-n plane.

The light beam L13 is obliquely incident on a surface 21A to be inspected of a substrate 21 to be inspected, which is placed on a stage 20, and linearly scans the surface 21A to be inspected of the substrate 21 to be inspected upon rotation of the optical unit 5 driven by the motor 1 of the optical scanning device 6 (more specifically, upon rotation of the reflection mirror 4).

In this case, as shown in FIG. 4, a plurality of light-receiving units 24A to 24C constituted by focusing lenses 22A to 22C and light-receiving elements 23A to 23C are disposed around the stage 20, so that scattered light generated upon scanning the surface 21A to be inspected of the substrate 21 to be inspected with the light beam L13 can be received from different space directions.

In practice, the positions of these light-receiving units 24A to 24C are selected, so that all the light-receiving elements 22A to 22C do not receive scattered light from the edge of a pattern formed on the surface 21A to be inspected of the substrate 21 to be inspected, in consideration of the fact that scattered light generated when the light beam L13 is irradiated onto the edge of the pattern formed on the surface 21A to be inspected of the substrate 21 to be inspected shows strong directivity, while scattered light generated by foreign matter scatters every directions.

Figure 5:
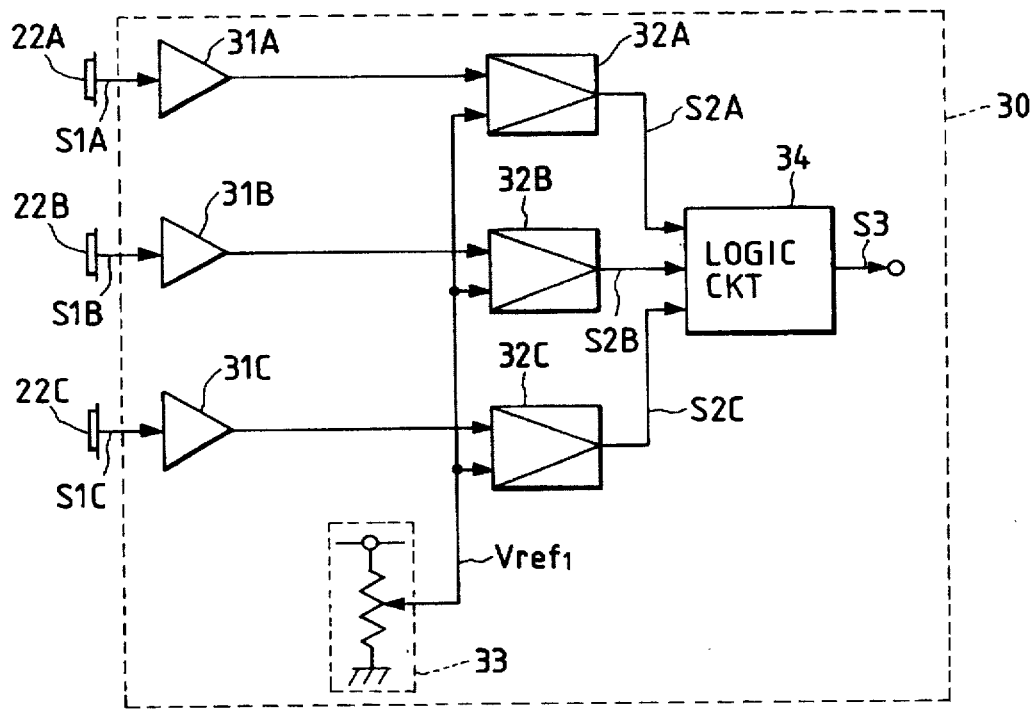
FIG. 5 is a block diagram showing the arrangement of a signal processing unit to be applied to the foreign matter inspection apparatus according to the first embodiment of the present invention.

Furthermore, as shown in FIG. 5, the outputs from these light-receiving elements 22A to 22C are supplied, as scattered light amount detection signals S1A to S1C, to corresponding differential amplifiers 32A to 32C via corresponding amplifiers 31A to 31C of a signal processing unit 30. These signals S1A to S1C are compared with a reference voltage $V_{ref1}$ supplied from a reference voltage supply unit 33 in the differential amplifiers 32A to 32C.

The comparison results output from these differential amplifiers 32A to 32C are supplied, as comparison signals S2A to S2C, to a logic circuit 34. At this time, the logic circuit 34 performs predetermined calculation processing such as a logical product (AND) calculation on the basis of the supplied comparison signals S2A to S2C, and outputs a foreign matter detection signal S3 when all the light-receiving elements 22A to 22C output scattered light amount detection signals S1A to S1C with sufficiently high level.

In this manner, the foreign matter inspection apparatus 10 can detect the presence/absence of foreign matter on a scanning line 25 (FIG. 4) formed by the light beam L13 on the surface 21A to be inspected of the substrate 21 to be inspected, on the basis of the foreign matter detection signal S3.

In FIGS. 3 and 4, the stage 20 is moved by an actuator 26, which is driven in synchronism with the motor 1 in the optical scanning device 6, in a direction indicated by an arrow a, perpendicular to the scanning direction of the light beam L13, every time the light beam L13 has completed scanning of the surface 21A to be inspected of the substrate 21 to be inspected. With this movement, the light beam L13 can scan the entire surface 21A to be inspected of the substrate 21 to be inspected.

Hence, the foreign matter inspection apparatus 10 can inspect the presence/absence of foreign matter over the entire surface 21A to be inspected of the substrate 21 to be inspected.

(1-3) Operation of First Embodiment

In the above arrangement, in the foreign matter inspection apparatus 10, a linearly polarized light beam L10 emitted by the laser beam source 11 is converted by the quarter-wave plate 12 into a circularly polarized light beam L11, and the light beam L11 enters the optical unit 5 of the optical scanning device 6 along the rotation axis K1 via the optical system constituted by the reflection mirror 13, the beam expander lens system EX, the lens 14, and the reflection mirror 15.

The light beam L11 is converted into a linearly polarized light beam L13, the plane of vibration of the electric vector of which is perpendicular to the z-n plane, by the quarter-wave plate 3 in the optical unit 5, and the light beam L13 is deflected by the reflection surface 4A of the reflection mirror 4, so that the beam L13 is incident on the surface 21A to be inspected of the substrate 21 to be inspected, and its exit direction rotates about the rotation axis K1.

Furthermore, scattered light generated on the surface 21A to be inspected of the substrate 21 to be inspected is received by the plurality of light-receiving elements 22A to 22C, and the signal processing unit 30 detects the presence/absence of foreign matter on the basis of the outputs from these light-receiving elements 22A to 22C.

Therefore, since this foreign matter inspection apparatus 10 uses neither a galvano mirror nor a polygonal mirror in the optical system unlike in the conventional foreign matter inspection apparatus, the inspection speed is not limited, and the optical performance can be prevented from lowering.

Since neither a galvano mirror nor a polygonal mirror are used in the optical system, no large-field angle focusing lens is required. Since the lens 15 whose field angle is not limited is used as the focusing lens, the design and manufacture of the optical system are facilitated.

Furthermore, in this foreign matter inspection apparatus 10, as described above, since the plane of vibration of the electric vector of the light beam L13 output from the optical unit 5 of the optical scanning device 6 is always perpendicular to the z-n plane irrespective of the rotation position of the optical unit 5, the light beam L13 can always be incident on the surface 21A to be inspected of the substrate 21 to be inspected as s-polarized light waves.

Therefore, the foreign matter inspection apparatus 10 can detect foreign matter with higher precision than the conventional foreign matter inspection apparatus that does not consider the polarization state of a light beam to be incident on the surface 21A to be inspected of the substrate 21 to be inspected.

(1-4) Effect of First Embodiment

With the above-mentioned arrangement, the optical scanning device 6 in which the quarter-wave plate 3 and the reflection mirror 4 are fixed to the drive shaft 1A of the motor 1 is arranged, a circularly polarized light beam L11 entering the optical scanning device 6 is converted by the quarter-wave plate 3 into a light beam L12, the direction of vibration of the electric vector of which is perpendicular to the z-n plane, and the light beam L12 is deflected by the reflection surface 4A of the reflection mirror 4 toward the surface 21A to be inspected of the substrate 21 to be inspected. Hence, the optical scanning device and the foreign matter inspection apparatus that can always scan the surface 21A to be inspected of the substrate 21 to be inspected with the light beam L13 consisting of s-polarized light wave at high speed, i.e., can scan a large area with a light beam in always a predetermined polarization state at high speed, can be realized. In this manner, the foreign matter inspection apparatus which has high inspection efficiency and precision and can cope with a large-scale substrate can be obtained.

(2) Second Embodiment (2-1) Principle

Figure 6A:
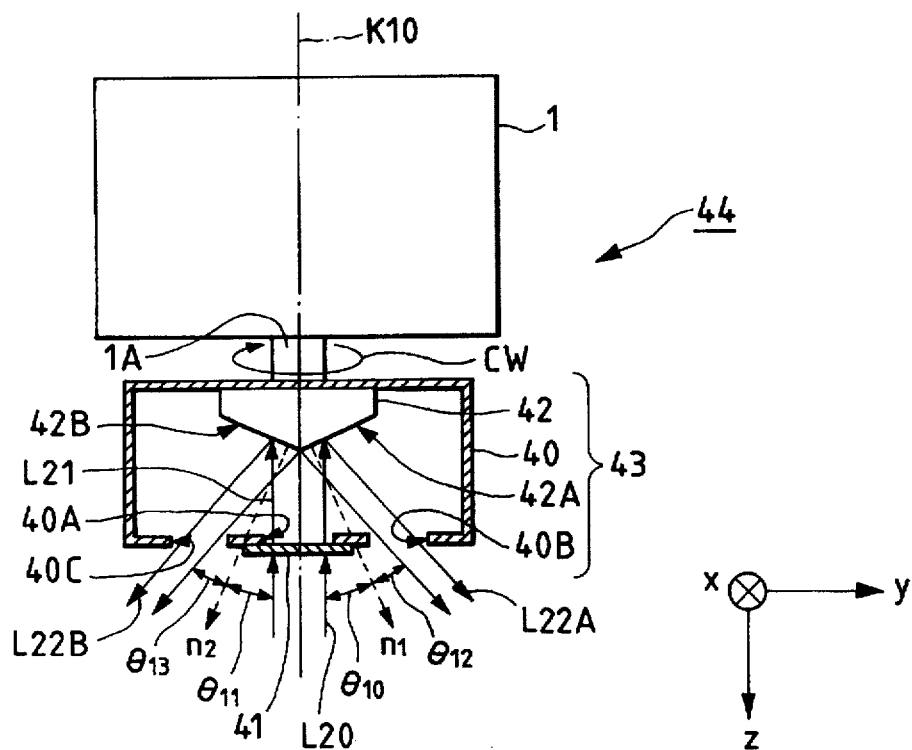
FIGS. 6A and 6B are respectively a front view and a bottom view showing the arrangement of an optical scanning device to be applied to a foreign matter inspection apparatus according to the second embodiment of the present invention.
Figure 6B:
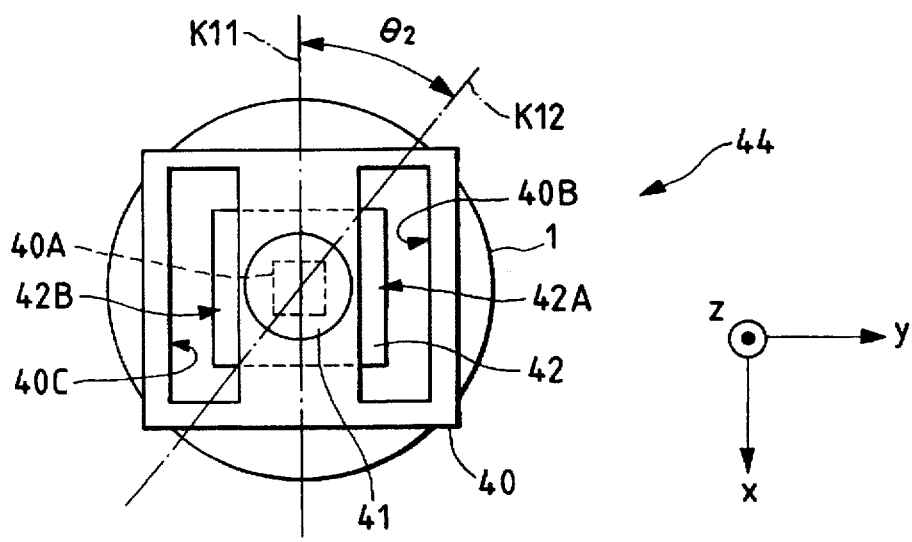

A case will be examined below wherein a right-circularly polarized light beam L20 enters, along an axis K10 parallel to the z-direction, an optical scanning device 44 in which an optical unit 43 constituted by a housing 40, a quarter-wave plate 41, and a reflection mirror 42 is fixed to a drive shaft 1A of a motor 1, as shown in FIGS. 6A and 6B.

In this case, assume that the motor 1 rotates, via the drive shaft 1A, the optical unit 43 in a direction indicated by an arrow CW about the rotation axis K10. In the optical unit 43, the quarter-wave plate 41 is fixed to the lower surface of the housing 40 to cover a window 40A formed on the bottom surface of the housing 40, and the reflection mirror 42 is fixed inside the housing 40, so that normals $n_1$ and $n_2$ to first and second reflection surfaces 42A and 42B are tilted respectively at predetermined angles $\theta_{10}$ and $\theta_{11}$ (in this embodiment, $\theta_{10}=\theta_{11}=22.5°$) with respect to the rotation axis K10.

At this time, a light beam L20 entering the optical unit 43 of the optical scanning device 44 is phase-modulated by the quarter-wave plate 41 to be converted into a light beam L21 consisting of linearly polarized light waves, and the light beam L21 is incident on the first and second reflection surfaces 42A and 42B of the reflection mirror 42 via the window 40A of the housing 40. The light beam L21 is then split into first and second light beams L22A and L22B by these first and second reflection surfaces 42A and 42B.

These first and second light beams L22A and L22B are reflected in directions that respectively form angles $\theta_{12}$ ($=\theta_{10}$) and $\theta_{13}$ ($=\theta_{11}$) with the normals $n_1$ and $n_2$ to the corresponding first and second reflection surfaces 42A and 42B of the reflection mirror 42, and exit the optical unit 42 via first and second windows 40B and 40C formed on the bottom surface of the housing 40, respectively.

Therefore, in the optical scanning device 44 as well, the first and second light beams L22A and L22B exit the optical unit 43 while rotating their exit directions about the rotation axis K1 upon rotation of the optical unit 43 (i.e., the reflection mirror 42) driven by the motor 1 as in the case described in the paragraphs of the principle in the first embodiment.

In this optical scanning device 44, a third plane that includes a line of intersection (to be referred to as first line K11 of intersection (FIG. 6B) hereinafter) between a first plane including the first reflection surface 42A of the reflection mirror 42 and a second plane including the second reflection surface 42B, and is perpendicular to the rotation axis K10 is assumed, and the quarter-wave plate 41 is disposed so that the first line K11 of intersection and an optic axis K12 of the quarter-wave plate 41 form an angle of 45° therebetween in the third plane.

In this case, the light beam L20 which enters the optical unit 43 of the optical scanning device 44 along the axis K10 is converted by the quarter-wave plate 41 into the linearly polarized light beam L21, the direction of vibration of an electric vector of which is in the x-z plane in FIG. 6A, and thereafter, the light beam L21 is reflected by the first and second reflection surfaces 42A and 42B of the reflection mirror 42 to be split into the first and second light beams L22A and L22A, as described above.

At this time, the exit direction of the first light beam L22A rotates about the rotation axis K10 upon rotation of the optical unit 43 (i.e., the reflection mirror 42). In this case, since the reflection mirror 42 and the quarter-wave plate 41 rotate together, the plane of vibration of the electric vector of the light beam L22A is always perpendicular to the z-$n_1$ plane.

Likewise, the exit direction of the first light beam L22B rotates about the rotation axis K10 upon rotation of the optical unit 43 (i.e., the reflection mirror 42). In this case, since the reflection mirror 42 and the quarter-wave plate 41 rotate together, the plane of vibration of the electric vector of the light beam L22B is always perpendicular to the z-$n_2$ plane.

Therefore, in this optical scanning device 44, the surface to be inspected, which is disposed to be perpendicular to the rotation axis K10, of a substrate to be inspected can be scanned with the first and second light beams L22A and L22B always having a predetermined polarization state (s-polarized light).

(2-2) Arrangement of Foreign Matter Inspection Apparatus of Second Embodiment

Figure 7:
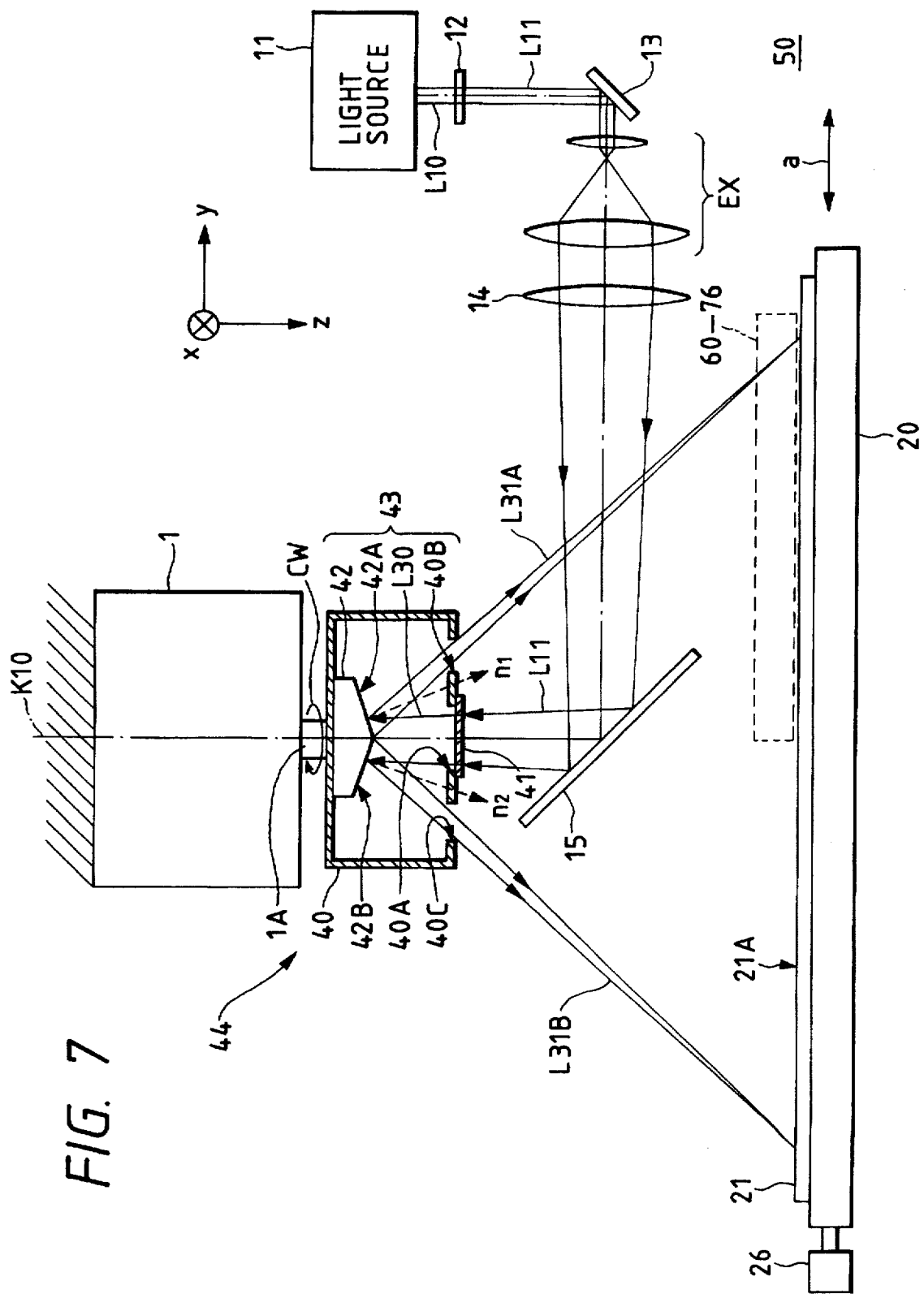
FIG. 7 is a side view showing the arrangement of the foreign matter inspection apparatus according to the second embodiment of the present invention.

Referring to FIG. 7 in which the same reference numerals denote corresponding portions in FIG. 3 and FIGS. 6A and 6B, reference numeral 50 indicates a foreign matter inspection apparatus according to the second embodiment as a whole. In this apparatus, a circularly polarized light beam L11 formed by phase-modulating, by a quarter-wave plate 12, a light beam L10 emitted by a laser beam source 11 enters the optical unit 43 of the optical scanning device 44 along the axis K10 parallel to the z-direction.

In this case, the quarter-wave plate 41 of the optical scanning device 44 is disposed, so that its optic axis K12 forms an angle $\theta_2$ ($=45°$) with the first line K11 of intersection in the third plane that includes the first line K11 of intersection and is perpendicular to the rotation axis K10.

In this manner, the light beam L11 entering the optical unit 43 of the optical scanning device 44 is converted by the quarter-wave plate 41 into a linearly polarized light beam L30 whose electric vector has a direction of vibration that agrees with the x-direction. Thereafter, the light beam L30 is split into first and second light beams L31A and L31B by the first and second reflection surfaces 42A and 42B of the reflection mirror 42, and these light beams L31A and LS1B exit the optical unit 42 via the corresponding windows 40B and 40C of the housing 40.

Figure 8:
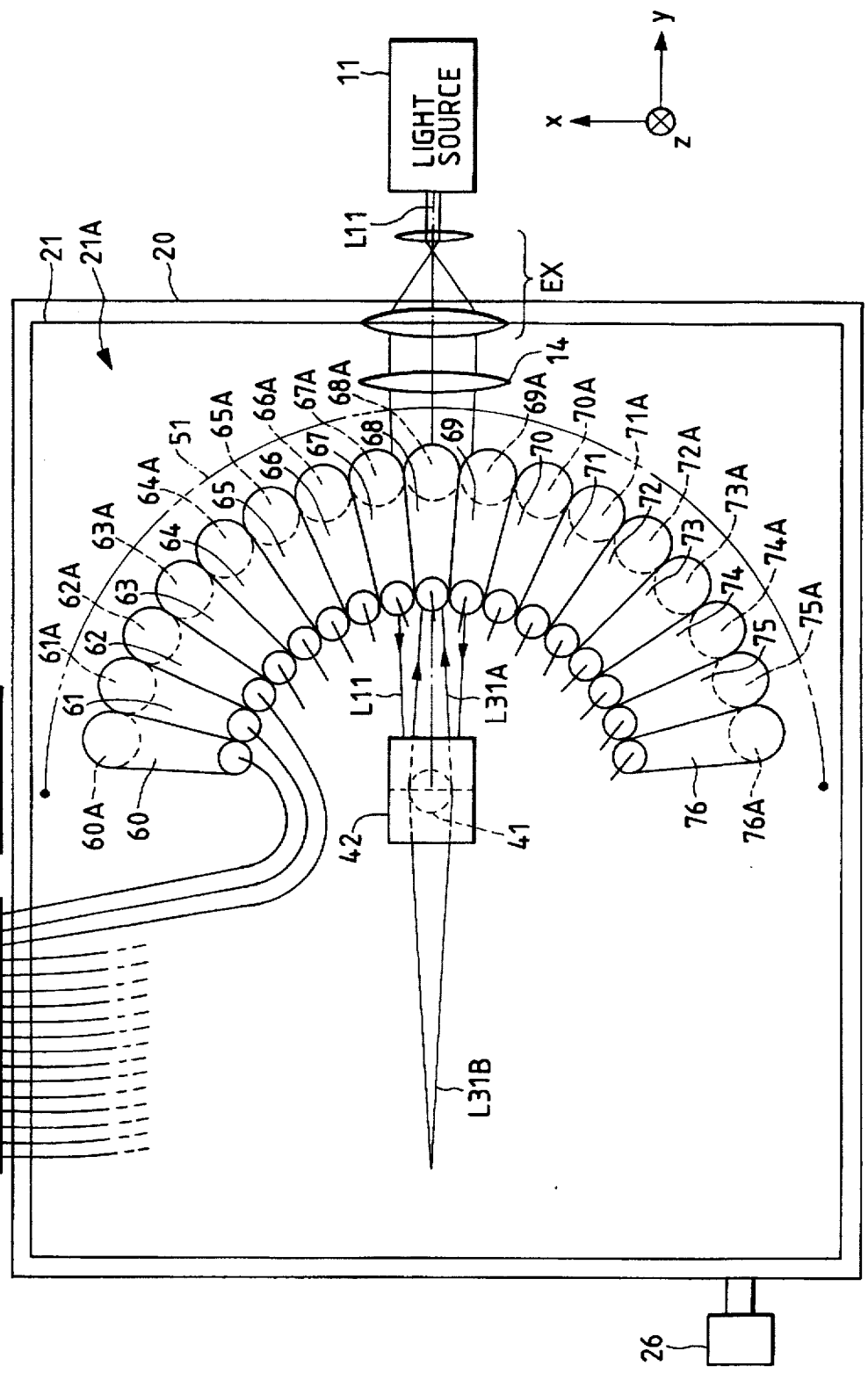
FIG. 8 is a plan view showing the arrangement of the foreign matter inspection apparatus according to the second embodiment of the present invention.

The first and second light beams L31A and L31B emerging from the optical scanning device 44 are respectively incident on a surface 21A to be inspected of a substrate 21 to be inspected disposed on a stage 20, so that the surface 21A to be inspected is located to be parallel to the x-y plane (i.e., perpendicular to the rotation axis K10), and alternately form an arcuated scanning line 51, as shown in FIG. 8, on the surface 21A to be inspected of the substrate 21 to be inspected upon rotation of the optical unit 43. In practice, the first and second light beams L31A and L31B scan the surface 21A to be inspected of the substrate 21 to be inspected in a circular pattern, but this foreign matter inspection apparatus 50 uses only a 180° arc portion shown in FIG. 8 of this circular pattern. For this reason, in the following description, the first and second light beams L31A and L31B alternately form the arcuated scanning line 51 on the surface 21A to be inspected of the substrate 21 to be inspected.

In this case, the stage 20 is sequentially moved a small distance in a direction indicated by an arrow a every time the first or second light beam L31A or L31B has completed formation of the scanning line 51 on the surface 21A to be inspected of the substrate 21 to be inspected. With this movement, in this foreign matter inspection apparatus 50, the first and second light beams L31A and L31B alternately form scanning lines 51 on the entire surface 21A to be inspected of the substrate 21 to be inspected.

Figure 9:
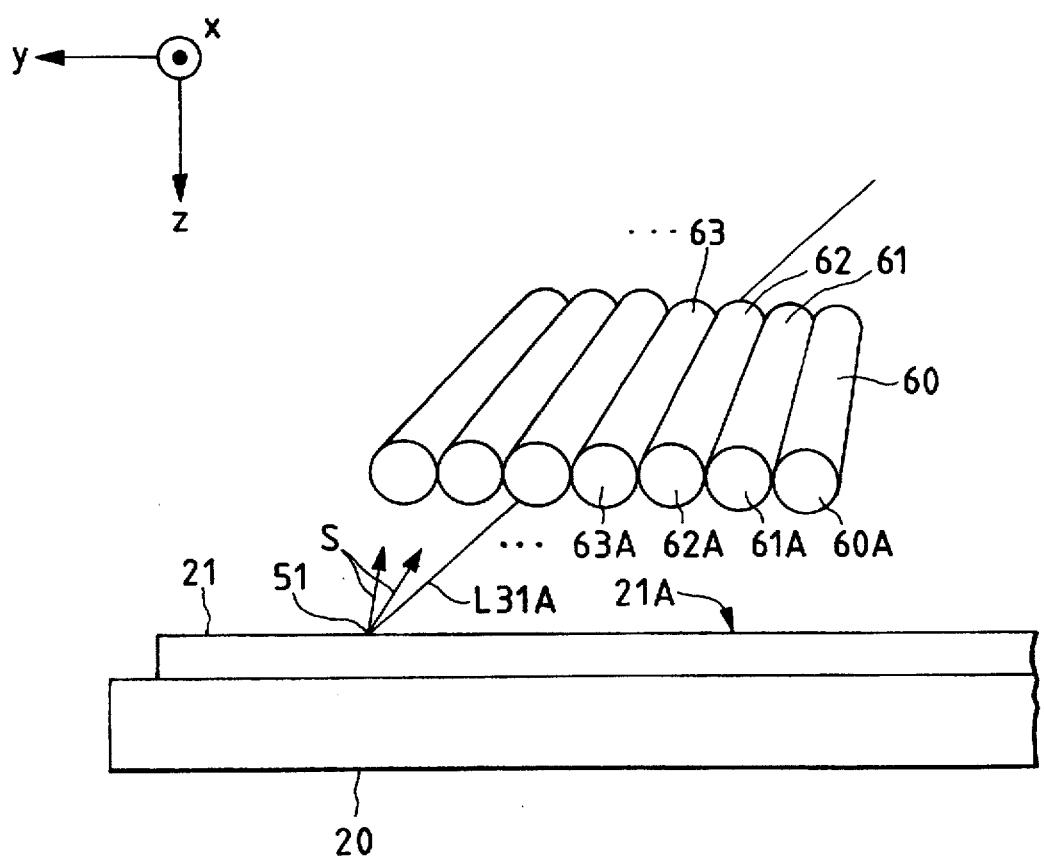
FIG. 9 is a partial side view showing the arrangement of the foreign matter inspection apparatus according to the second embodiment of the present invention.

On the other hand, a plurality of light-receiving elements 60 to 76 comprising, e.g., photomultipliers are disposed at equal intervals above the stage 20, so as to observe the scanning line 51 formed by the first and second light beams L31A and L31B on the surface 21A to be inspected of the substrate 21 to be inspected from the above, as shown in FIGS. 8 and 9.

At this time, light-receiving surfaces 60A to 76A of the light-receiving elements 60 to 76 are disposed in an arcuated pattern to oppose the scanning line 51, so as to receive scattered light S (FIG. 9) from a portion of the scanning line 51. In addition, the observation field (photometry region) of each of these light-receiving elements 60 to 67 overlaps the observation fields of two neighboring ones of the light-receiving elements 60 to 76, so that scattered light S from any point on the scanning line 51 can be received by three adjacent ones of the light-receiving elements 60 to 76.

Figure 10:
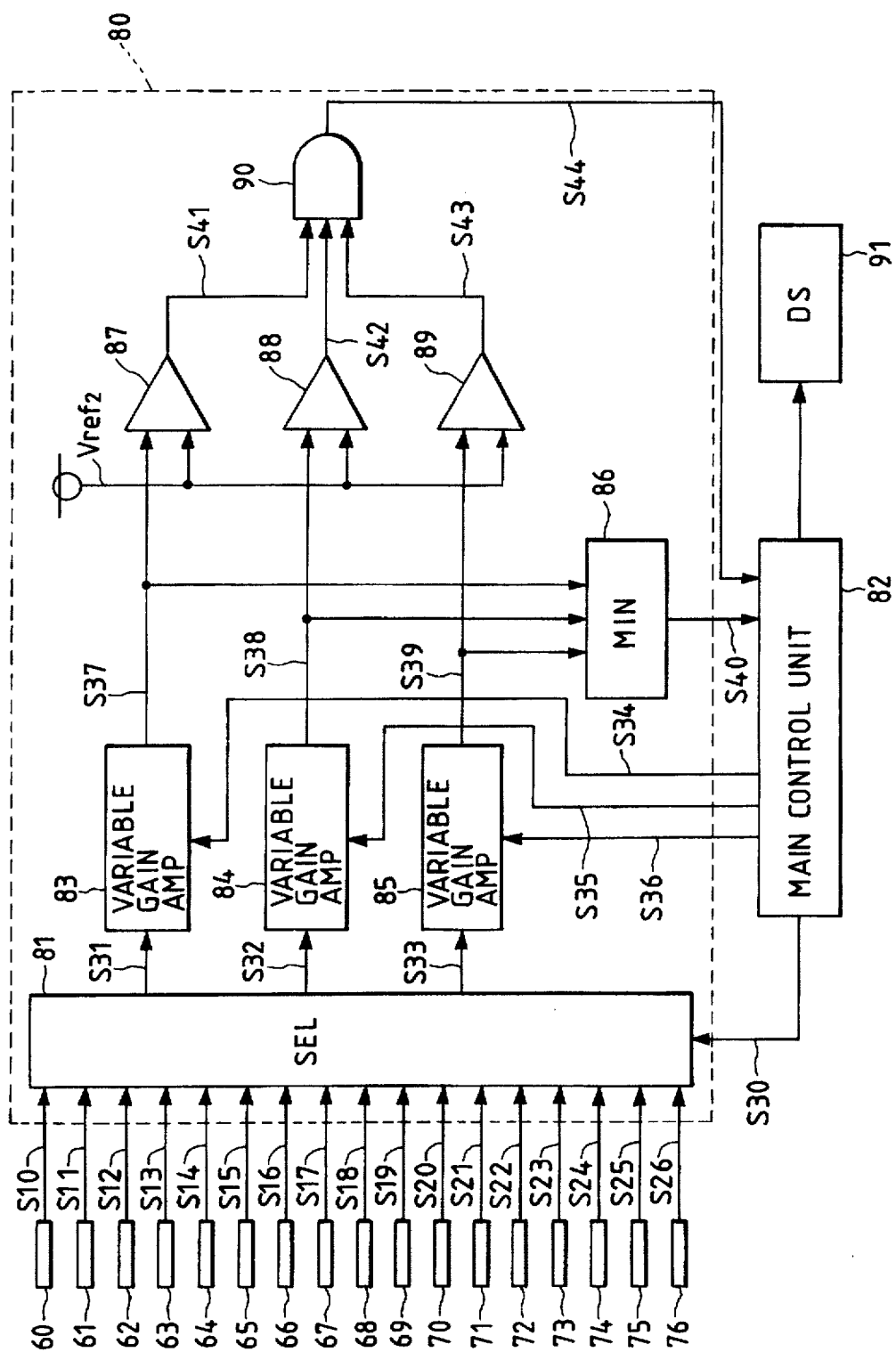
FIG. 10 is a block diagram showing the arrangement of a signal processing unit to be applied to the foreign matter inspection apparatus according to the second embodiment of the present invention.

Scattered light amount detection signals S10 to S26 having signal levels corresponding to the light-receiving amounts output from these light-receiving elements 60 to 76 are supplied to a signal switching circuit 81 of a signal processing unit 80, which has an arrangement, as shown in FIG. 10.

The signal switching circuit 81 selects three light-receiving elements that can receive scattered light S from an inspection point corresponding to the rotation angle from the 17 light-receiving elements 60 to 76 on the basis of rotation angle information S30 of the optical unit 43 (FIG. 7) of the optical scanning device 44 (FIG. 7), which information is supplied from a rotary encoder (not shown) via a main control unit 82. Then, the circuit 81 outputs the scattered light amount detection signals output from the three selected light-receiving elements to first to third variable gain amplifiers 83 to 85 as selection signals S31 to S33.

In this case, the signal levels of the scattered light amount detection signals output from these three selected light-receiving elements change depending on the generation position of scattered light S, i.e., the scanning position (or the rotation angle of the optical unit 43) of the light beam L31A or L31B (FIG. 7) even when the light amount of scattered light S generated in the photometry region is constant.

For this reason, when the light amount of scattered light generated in the photometry region of the central one of the three neighboring light-receiving elements is constant, the first to third variable gain amplifiers 83 to 85 change their gains on the basis of rotation angle information signals S34 to S36 of the optical unit 43 supplied from the main control unit 82, so that the scattered light amount detection signals supplied from these three light-receiving elements have the same signal level independently of the rotation angle of the optical unit 43, and output correction signals S37 to S39 obtained upon changing the gains to a minimum value selection circuit 86.

The minimum value selection circuit 86 selects a minimum signal value of the supplied correction signals S37 to S39, and outputs the selected signal to the main control unit 82 as a minimum value signal S40. The main control unit 82 specifies the size of foreign matter on the basis of the received minimum value. In this case, the reason why the minimum value is used for specifying the size of foreign matter is to remove noise from the edge when the pattern edge and foreign matter are both present.

The correction signals S37 to S39 output from the first to third variable gain amplifiers 83 to 85 are also parallelly supplied to corresponding first to third comparators 87 to 89.

These first to third comparators 87 to 89 binarize the correction signals S37 to S39 by comparing them with a threshold value $V_{ref2}$, which has a sufficiently high level in consideration of the levels of electrical noise and optical noise, and output the binarized signals to an AND gate 90 as binary correction signals S41 to S43.

The AND gate 90 outputs a foreign matter detection signal S44 to the main control unit 82 when all the received binary correction signals S41 to S43 exceed the threshold value $V_{ref2}$.

The main control unit 82 fetches the minimum value from the minimum value selection circuit 86 in response to the foreign matter detection signal S44 as a trigger signal, and determines the size of foreign matter on the basis of the fetched minimum value. Furthermore, the main control unit 82 displays the size, shape, and the like of foreign matter on a display 91 together with the foreign matter position on the surface 21A to be inspected of the substrate 21 to be inspected.

In this manner, the foreign matter detection apparatus 50 can detect and display the position, shape, and the like of foreign matter attached to the surface 21A to be inspected of the substrate 21 to be inspected placed on the stage 20.

(2-3) Operation of Second Embodiment

In this arrangement, in the foreign matter detection apparatus 50, a light beam L10 emitted by the laser beam source 11 is converted by the quarter-wave plate 12 into a circularly polarized light beam L11, and the light beam L11 enters the optical unit 43 of the optical scanning device 44 along the rotation axis K10 via the optical system constituted by the reflection mirror 13, the beam expander lens system EX, the lens 14, and the reflection mirror 15.

The light beam L11 is converted by the quarter-wave plate 41 of the optical unit 43 into a linearly polarized light beam L30, the direction of vibration of the electric vector of which is parallel to both the first and second reflection surfaces 42A and 42B of the reflection mirror 42. Thereafter, the light beam L30 is reflected by the first and second reflection surfaces 42A and 42B of the reflection mirror 42 and the reflected light beams are incident on the surface 21A to be inspected of the substrate 21 to be inspected, thus forming an arcuated scanning line 51 upon rotation of the optical unit 43.

Furthermore, scattered light S generated on the surface 21A to be inspected of the substrate 21 to be inspected is received by the plurality of light-receiving elements 60 to 76 disposed in the arcuated pattern along the scanning line 51, and the signal processing unit 80 and the main control unit 82 detect the presence/absence of foreign matter on the basis of scattered light amount detection signals S10 to S26 output from the light-receiving elements 60 to 76. Thereafter, the detection result is displayed on the display 91.

Therefore, since this foreign matter inspection apparatus 50 uses neither a galvano mirror nor a polygonal mirror in the optical system as in the foreign matter inspection apparatus 10 (FIG. 3) of the first embodiment, the inspection speed is not limited, and the optical performance can be prevented from lowering.

In the foreign matter inspection apparatus 50, as described above, since the planes of vibration of the electric vectors of the first and second light beams L31A and L31B emerging from the optical unit 43 of the optical scanning device 44 are perpendicular to the z-$n_1$ and z-$n_2$ planes irrespective of the rotation position of the optical unit 43, these first and second light beams L31A and L31B can be incident on the surface 21A to be inspected of the substrate 21 to be inspected always as s-polarized light waves. Therefore, the foreign matter inspection apparatus 50 can detect foreign matter with high precision as in the foreign matter inspection apparatus 10 (FIG. 3) of the first embodiment.

Furthermore, in this foreign matter inspection apparatus 50, the light beam L11 entering the optical unit 43 is split into two beams, i.e., the first and second light beams L31A and L31B, and the surface 21A to be inspected of the substrate 21 to be inspected is alternately scanned with these first and second light beams L31A and L31B. For this reason, the foreign matter inspection apparatus 50 can perform foreign matter scanning at higher speed than the foreign matter inspection apparatus 10 (FIG. 3) of the first embodiment.

(2-4) Effect of Second Embodiment

With the above-mentioned arrangement, the optical scanning device 44 in which the quarter-wave plate 41 and the reflection mirror 42 with the first and second reflection surfaces 42A and 42B are fixed to the drive shaft 1A of the motor 1 is arranged, a circularly polarized light beam L11 entering the optical scanning device 44 is converted by the quarter-wave plate into a light beam L30, the direction of vibration of the electric vector of which is perpendicular to the z-$n_1$ plane (and the z-$n_2$ plane), the light beam L30 is split into first and second light beams L31A and L31B by the first and second reflection surfaces 42A and 42B of the reflection mirror 42 so as to be deflected toward the surface 21A to be inspected of the substrate 21 to be inspected. Hence, the polarization state of the first and second light beams L31A and L31B incident on the surface 21A to be inspected of the substrate 21 to be inspected can always be s-polarized light, and these first and second light beams L31A and L31B can scan the surface 21A to be inspected of the substrate 21 to be inspected at high speed. Therefore, the optical scanning device and the foreign matter inspection apparatus that can scan a large area at high speed with a light beam always having a predetermined polarization state can be realized. In this manner, the foreign matter inspection apparatus which has high inspection efficiency and precision and can cope with a large-scale substrate can be realized.

(3) Third Embodiment (3-1) Principle

Figure 11A:
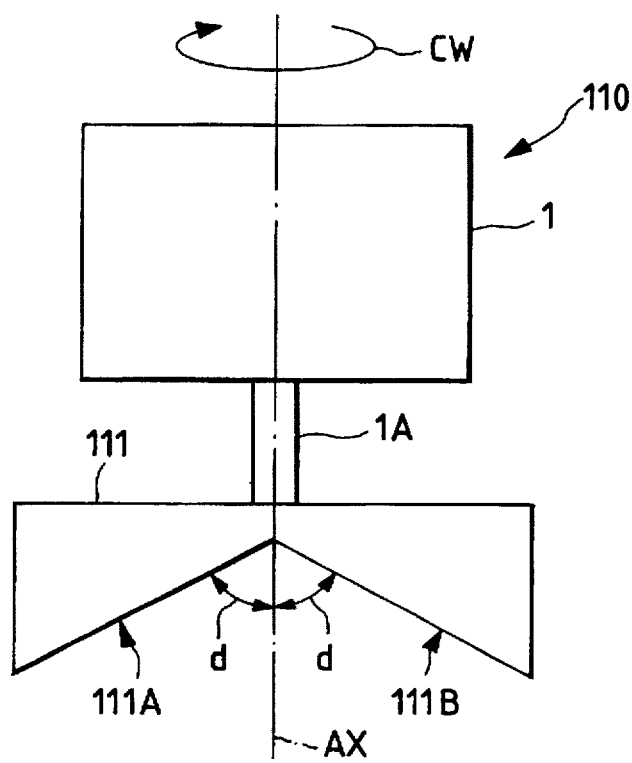
FIGS. 11A and 11B are respectively a side view and a bottom view showing the arrangement of an optical scanning device to be applied to a foreign matter inspection apparatus according to the third embodiment of the present invention.
Figure 11B:
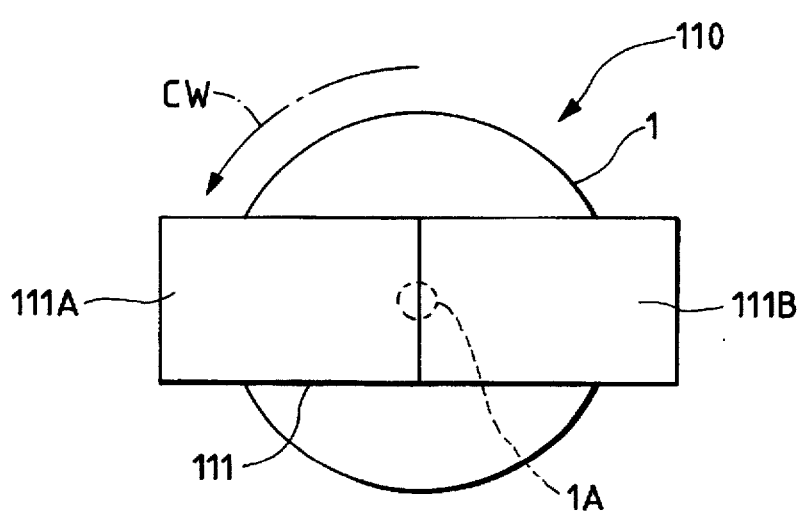

In FIGS. 11A and 11B in which the same reference numerals denote corresponding portions in FIGS. 6A and 6B, in an optical scanning device 110 according to the third embodiment, first and second reflection surfaces 111A and 111B constituted by two plane mirrors of a rotary mirror 111 make an identical angle d with respect to an optical axis AX parallel to a drive shaft 1A of a motor 1.

Figure 12:
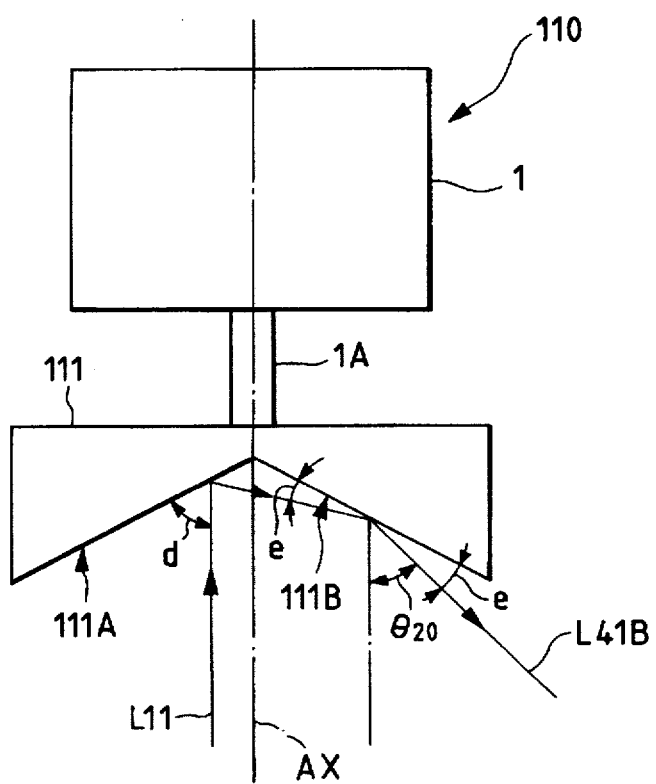
FIG. 12 is a side view showing the state of a reflected light beam in a normal state in the optical scanning device shown in FIGS. 11A and 11B.

FIG. 12 shows the relationship between an incident light beam L11 incident along the optical axis AX, and a second reflected light beam L41B when the drive shaft 1A of the motor 1 does not cause any axial run-out with respect to the optical axis AX. In this case, the incident light beam L11 is reflected by the first reflection surface 111A, is then reflected by the second reflection surface 111B, and propagates as a second reflected light beam L41B.

The incident light beam L11 forms an angle d with respect to the first reflection surface 111A since it is parallel to the optical axis AX. Hence, let e be the angle formed between the second reflected light beam L41B and the second reflection surface 111B. Then, the angle e is geometrically expressed by equation (1) below:

$$e = \pi - 3d \tag{1}$$

Therefore, when $\theta_{20}$ represents the angle formed between the second reflection light beam L41B and the optical axis AX, the angle $\theta_{20}$ is given by:

$$\theta_{20} = d - e = 4d - \pi \tag{2}$$

Figure 13:
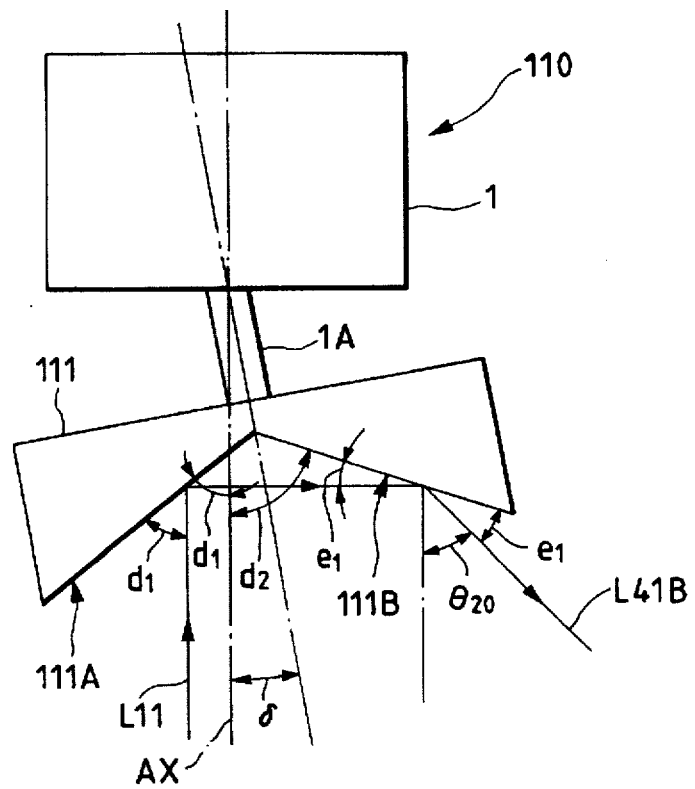
FIG. 13 is a side view showing the state of a reflected light beam in an axial run-out state in the optical scanning device shown in FIGS. 11A and 11B.

FIG. 13 shows a case wherein the drive shaft 1A of the motor 1 statically or dynamically causes an axial run-out with respect to the optical axis AX, and consequently, the drive shaft 1A is tilted at an angle $\delta$ with respect to the optical axis AX.

In this case, the incident light beam L11 parallel to the optical axis AX forms an angle $d_1$ with the first reflection surface 111A, and when $d_2$ represents the angle formed between the optical axis AX and the second reflection surface 111B, the relationship between the angles $d_1$ and $d_2$ is given by:

$$d_1 + d_2 = 2d \tag{3}$$

Let $e_1$ be the angle formed between the second reflected light beam L41B and the second reflection surface 111B. Then, the angle $e_1$ is geometrically expressed by equation (4) below obtained by substituting equation (3) above:

$$e_1 = \pi - 2d_1 - d_2 = \pi - 2d_1 + (d_1 - 2d) = \pi - d_1 - 2d \tag{4}$$

Furthermore, the angle $\theta_{20}$ of the second reflected light beam L41B with respect to the optical axis AX is expressed by equation (5) below obtained by substituting equations (3) and (4) above:

$$\theta_{20} = d_2 - e_1 = (2d - d_1) - (\pi - d_1 - 2d) = 4d - \pi \tag{5}$$

As can be seen from the above equations, the angle $\theta_{20}$ of the second reflected light beam L41B with respect to the optical axis AX always exhibits a constant value irrespective of the value of the tilt angle $\delta$ when the drive shaft 1A of the motor 1 tilts with respect to the optical axis AX. As a result, even when the drive shaft 1A of the motor 1 statically or dynamically causes an axial run-out with respect to the optical axis AX, the second reflected light beam L41B can be prevented from being influenced by a surface run-out of the second reflection surface 111B. As in the above-mentioned case, when the incident light beam L11 is incident on the second reflection surface 111B, a first reflected light beam L41A can be prevented from being influenced by a surface run-out of the first reflection surface 111A.

(3-2) Arrangement of Foreign Matter Inspection Apparatus According to Third Embodiment A foreign matter inspection apparatus to which the optical scanning device 110 is applied will be explained below with reference to FIG. 14. Note that the same reference numerals in FIG. 14 denote corresponding portions as those in FIG. 7.

Figure 14:
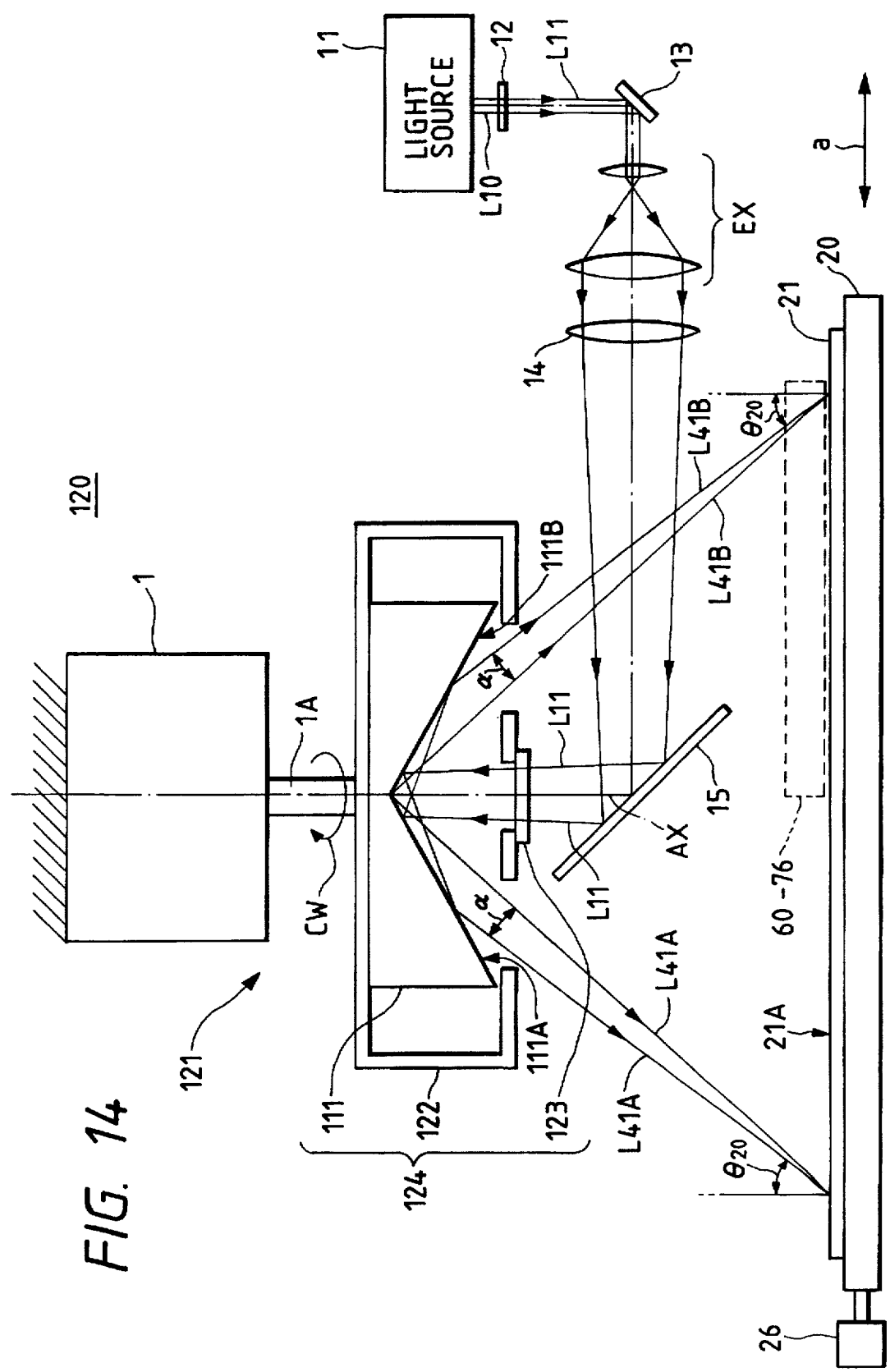
FIG. 14 is a side view showing the arrangement of the foreign matter inspection apparatus according to the third embodiment of the present invention.

In a foreign matter inspection apparatus 120 shown in FIG. 14, an optical unit 124 constituted by a housing 122 and a quarter-wave plate 123 is arranged to be rotatable in a direction indicated by an arrow CW together with the drive shaft 1A of the motor 1.

In the optical unit 124, the rotary mirror 111 is fixed to the upper inner surface of the housing 122, and the quarter-wave plate 123 is fixed to the lower outer surface of the housing 122 to cover a window formed coaxially with the drive shaft 1A.

In this foreign matter inspection apparatus 120, a light beam L10 emitted by a laser beam source 11 and consisting of linearly polarized light waves is phase-modulated to circularly polarized light waves via a quarter-wave plate 12, and the modulated light beam is reflected by a reflection mirror 13 to become incident on a beam expander lens system EX. After the light beam is expanded by the beam expander lens system EX, the light beam enters the optical unit 124 via a reflection mirror 15 fixed inside the apparatus as an incident light beam L11 focused at a predetermined aperture angle $\alpha$ via a lens 14.

The incident light beam L11 entering the optical unit 124 is phase-modulated by the quarter-wave plate 123 into linearly polarized light waves, the direction of vibration of an electric vector of which is perpendicular to a plane z-$AX_1$ or z-$AX_2$ including the optical axis AX and the first or second reflection surface 111A or 111B.

Thereafter, the light beam is reflected by the first and second reflection surfaces 111A and 111B of the rotary mirror 111, and reflected light beams are incident, as first and second reflected light beams L41A and L41B consisting of s-polarized light waves, on a surface 21A to be inspected of a substrate 21 placed on a stage 20, via windows formed on the lower surface of the housing 122. At this time, the first and second reflected light beams L41A and L41B scan the surface 21A to be inspected of the substrate 21 to be inspected in an arcuated pattern upon rotation of the optical unit 124 driven by the motor 1, as in the second embodiment described above.

The stage 20 on which the substrate 21 to be inspected is placed is moved in a direction indicated by an arrow a by an actuator 26 which is driven in synchronism with the motor 1, every time the optical unit 124 rotates 180°. With this movement, the first and second reflected light beams L41A and L41B can scan the entire surface 21A to be inspected of the substrate 21 to be inspected.

As in the second embodiment described above, a plurality of light-receiving units 60 to 76, which comprise focusing lenses and light-receiving elements and are the same as those used in the second embodiment, are juxtaposed in an arcuated pattern at equal intervals to obliquely look into the optical scanning line, so as to receive scattered light generated on the surface 21A to be inspected from different space directions when the first and second reflected light beams L41A and L41B scan the surface 21A to be inspected of the substrate 21 to be inspected. Furthermore, as in the second embodiment, a signal processing unit and a main control unit (neither are shown) for processing the light-receiving results of these light-receiving units are arranged. Note that the light-receiving units, signal processing unit, and main control unit applied to the third embodiment are the same as those in the second embodiment, and a detailed description thereof will be omitted.

(3-3) Operation of Third Embodiment

In the above arrangement, in this foreign matter inspection apparatus 120, a light beam L10 emitted by the laser beam source 11 and consisting of linearly polarized light waves is phase-modulated into circularly polarized light waves by the quarter-wave plate 12, and thereafter, the modulated light beam enters the optical unit 124 of an optical scanning device 121 via the optical system constituted by the reflection mirror 13, the beam expander lens system EX, the lens 14, and the reflection mirror 15, so that the drive shaft 1A of the motor 1 agrees with the optical axis AX.

This incident light beam L11 is converted by the quarter-wave plate 123 in the optical unit 124 into a light beam consisting of linearly polarized light waves, and the converted light beam is reflected by the first and second reflection surfaces 111A and 111B of the rotary mirror 111 toward the surface 21A to be inspected of the substrate 21 to be inspected. At the same time, the optical unit 124 is rotated by driving the motor 1. With this operation, first and second reflected light beams L41A and L41B scan the surface 21A to be inspected of the substrate 21 to be inspected.

Furthermore, scattered light generated on the surface 21A to be inspected of the substrate 21 to be inspected at that time is received by the light-receiving units 60 to 76 having a plurality of light-receiving elements as in the second embodiment, and a signal processing unit 80 detects the presence/absence of foreign matter on the basis of the outputs from these light-receiving units 60 to 76.

Furthermore, in this foreign matter inspection apparatus 120, as described above, the incident light beam L11 to be output from the optical scanning device 121 is phase-modulated into linearly polarized light waves, the direction of vibration of the electric vector of which is perpendicular to the plane z-$AX_1$ or z-$AX_2$ including the optical axis AX and the first or second reflection surface 111A or 111B, and hence, the first and second reflected light beams L41A and L41B are incident on the surface 21A to be inspected of the substrate 21 to be inspected always as s-polarized light waves irrespective of the rotation angle of the optical unit 124 of the optical scanning device 121.

In this case, when the substrate 21 to be inspected consists of a glass material as in a liquid crystal substrate, the substrate has a higher reflectance for s-polarized light waves than that for p-polarized light waves. On the other hand, when a pattern consisting of a metal material is formed on the surface 21A to be inspected of the substrate 21 to be inspected, scattered light of p-polarized light waves is generated at the edge of the pattern more easily than that of s-polarized light waves, as is well known. Therefore, this foreign matter inspection apparatus 120 can inspect foreign matter with higher precision than the conventional foreign matter inspection apparatus that does not consider any polarization state of the light beam to be incident on the surface 21A to be inspected of the substrate 21 to be inspected.

Since the rotary mirror 111 is constituted by two plane mirrors serving as the first and second reflection surfaces 111A and 111B which do not form right angles therebetween, when the drive shaft 1A of the motor 1 causes a static or dynamic axial run-out, the angles formed by the first and second reflected light beams L41A and L41B with respect to the optical axis AX are determined by the angle formed between the first and second reflection surfaces 111A and 111B, and hence, they always exhibit a constant value irrespective of the degree of deviation of the drive shaft 1A with respect to the optical axis AX. As a result, even when the drive shaft 1A of the motor 1 statically or dynamically causes an axial run-out with respect to the optical axis AX, the first and second reflected light beams L41A and L41B are optically scanned without being influenced by surface run-outs of the first and second reflection surfaces 111A and 111B.

(3-4) Effect of Third Embodiment

With the above-mentioned arrangement, an incident light beam L11 consisting of circularly polarized light waves is converted by the quarter-wave plate 123 into first and second reflected light beams L41A and L41B having a predetermined polarization state, i.e., consisting of linearly polarized light waves, and the first and second reflected light beams L41A and L41B are deflected by the rotary mirror 111 to be incident on the surface 21A to be inspected of the substrate 21 to be inspected. Also, the first and second reflected light beams L41A and L41B scan the surface 21A to be inspected of the substrate 21 to be inspected by rotating the quarter-wave plate 123 and the rotary mirror 111 about the optical axis AX of the incident light beam L11 as the rotation shaft 1A. Hence, the apparatus can cope with a large-scale substrate 21 to be inspected, and can detect foreign matter with high precision.

Furthermore, since the rotary mirror 111 is constituted by two plane mirrors serving as the first and second reflection surfaces 111A and 111B that do not form right angles therebetween, even when the drive shaft 1A of the motor 1 causes a static or dynamic axial run-out, the first and second reflected light beams L41A and L41B are determined by the angles formed between the first and second reflection surfaces 111A and 111B, and hence, a foreign matter inspection apparatus that can optically scan the first and second reflected light beams L41A and L41B without being influenced by surface run-outs of the first and second reflection surfaces 111A and 111B can be realized.

(4) Fourth Embodiment (4-1) Principle

Figure 15A:
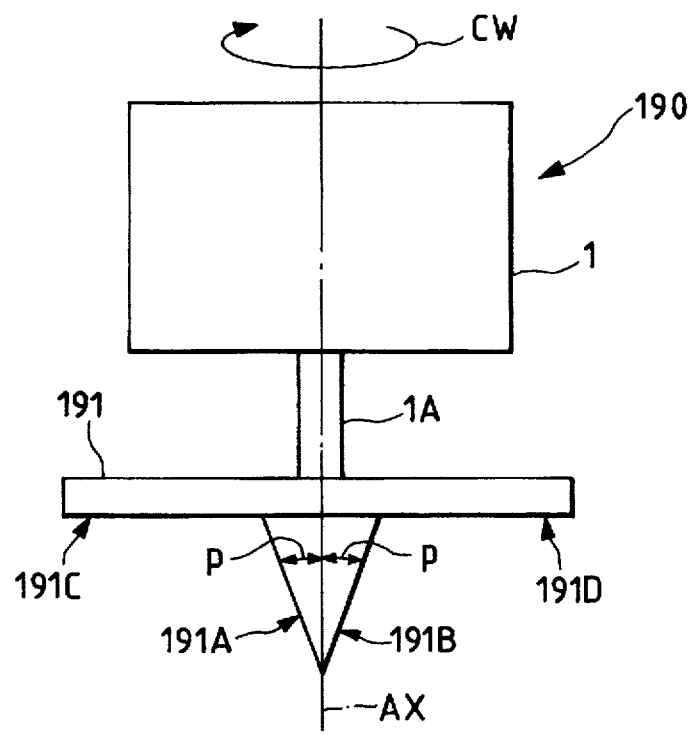
FIGS. 15A and 15B are respectively a side view and a bottom view showing the arrangement of an optical scanning device according to the fourth embodiment of the present invention.
Figure 15B:
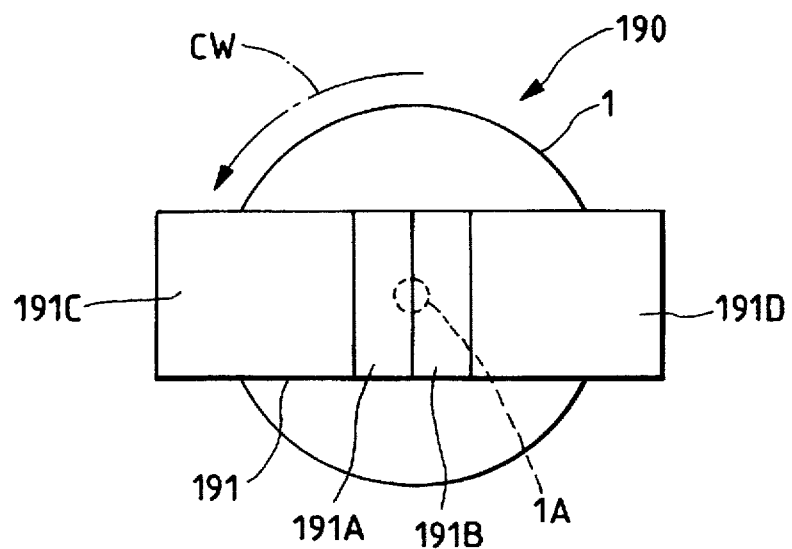

Referring to FIGS. 15A and 15B in which the same reference numerals denote corresponding portions as in FIGS. 11A and 11B, in an optical scanning device 190, a rotary mirror 191 is constituted by first to fourth reflection surfaces 191A to 191D comprising four plane mirrors, the first and second reflection surfaces 191A and 191B form an identical angle p with respect to an optical axis AX parallel to a drive shaft 1A of a motor 1, and the third and fourth reflection surfaces 191C and 191D form an identical plane perpendicular to the optical axis AX, unlike in the optical scanning device 110 of the third embodiment.

Figure 16:
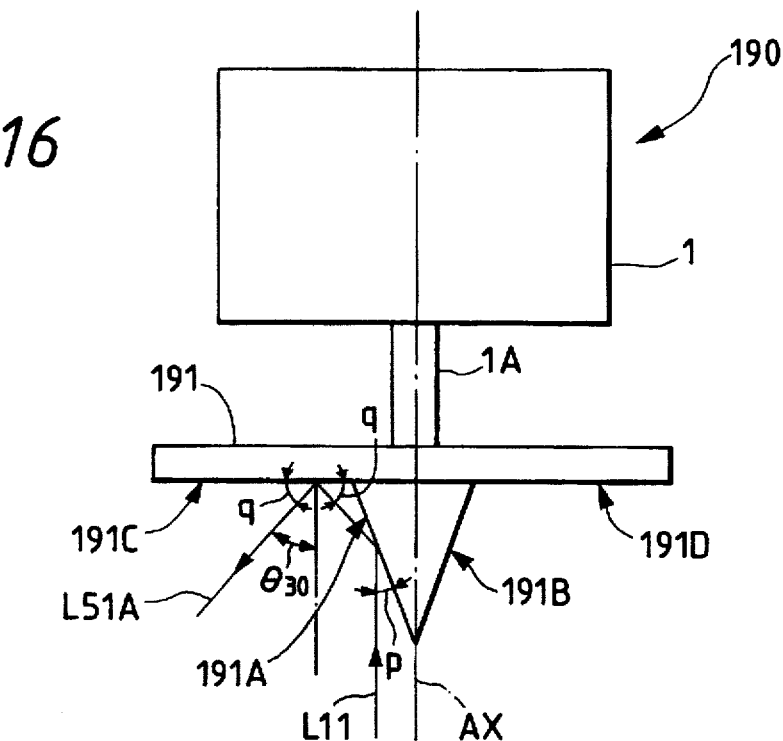
FIG. 16 is a side view showing the state of a reflected light beam in a normal state in the optical scanning device shown in FIGS. 15A and 15B.

FIG. 16 shows the relationship between an incident light beam L11 incident along the optical axis AX and a first reflected light beam L51A when the drive shaft 1A of the motor 1 does not cause any axial run-out with respect to the optical axis AX. In this case, the incident light beam L11 is reflected by the first reflection surface 191A, is then reflected by the third reflection surface 191C, and propagates as the first reflected light beam L51A.

The incident light beam L11 forms an angle p with respect to the first reflection surface 191A since it is parallel to the optical axis AX, and hence, when q represents the angle formed between the first reflected light beam L51A and the third reflection surface 191C, the angle q is geometrically given by:

$$q = \pi/2 - 2p \tag{6}$$

Therefore, letting $\theta_{30}$ be the angle formed between the first reflected light beam L51A and the optical axis AX, the angle $\theta_{30}$ is given by:

$$\theta_{30} = \pi/2 - q = \pi/2 - (\pi/2 - 2p) = 2p \tag{7}$$

Figure 17:
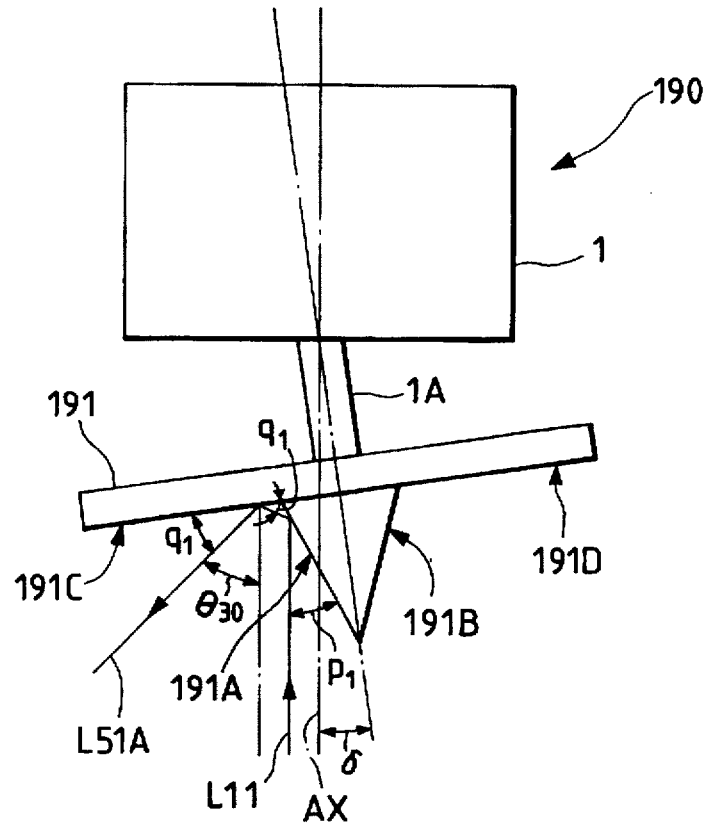
FIG. 17 is a side view showing the state of a reflected light beam in an axial run-out state in the optical scanning device shown in FIGS. 15A and 15B.

FIG. 17 Shows a case wherein the drive shaft 1A of the motor 1 statically or dynamically causes an axial run-out with respect to the optical axis AX, and the drive shaft 1A is tilted at an angle $\delta$ with respect to the optical axis AX.

In this case, when $p_1$ represents the angle formed by the incident light beam L11 parallel to the optical axis AX with respect to the first reflection surface 191A, the angle $p_1$ is given by:

$$p_1 = p + \delta \tag{8}$$

On the other hand, when $q_1$ represents the angle formed between the first reflected light beam L51A and the third reflection surface 191C, the angle $q_1$ is given by:

$$q_1 = \pi/2 - p - p_1 = \pi/2 - p - (p+\delta) = \pi/2 - 2p - \delta \tag{9}$$

Furthermore, the angle $\theta_{30}$ of the first reflected light beam L51A with respect to the optical axis AX is expressed by equation (10) below obtained by substituting equations (8) and (9):

$$\theta_{30} = \pi/2 - q_1 - \delta = \pi/2 - (\pi/2 - 2p - \delta) - \delta = 2p \tag{10}$$

As can be seen from the above equations, the angle $\theta_{30}$ of the first reflected light beam L51A with respect to the optical axis AX always exhibits a constant value irrespective of the value of the tilt angle $\delta$ when the drive shaft 1A of the motor 1 tilts with respect to the optical axis AX. As a result, even when the drive shaft 1A of the motor 1 statically or dynamically causes an axial run-out with respect to the optical axis AX, the first reflected light beam L51A can be prevented from being influenced by surface run-outs of the first and third reflection surfaces 191A and 191C. Likewise, when the incident light beam L11 is incident on the second reflection surface 191B, a second reflected light beam L51B can be prevented from being influenced by surface run-outs of the second and fourth reflection surfaces 191B and 191D.

Figure 18:
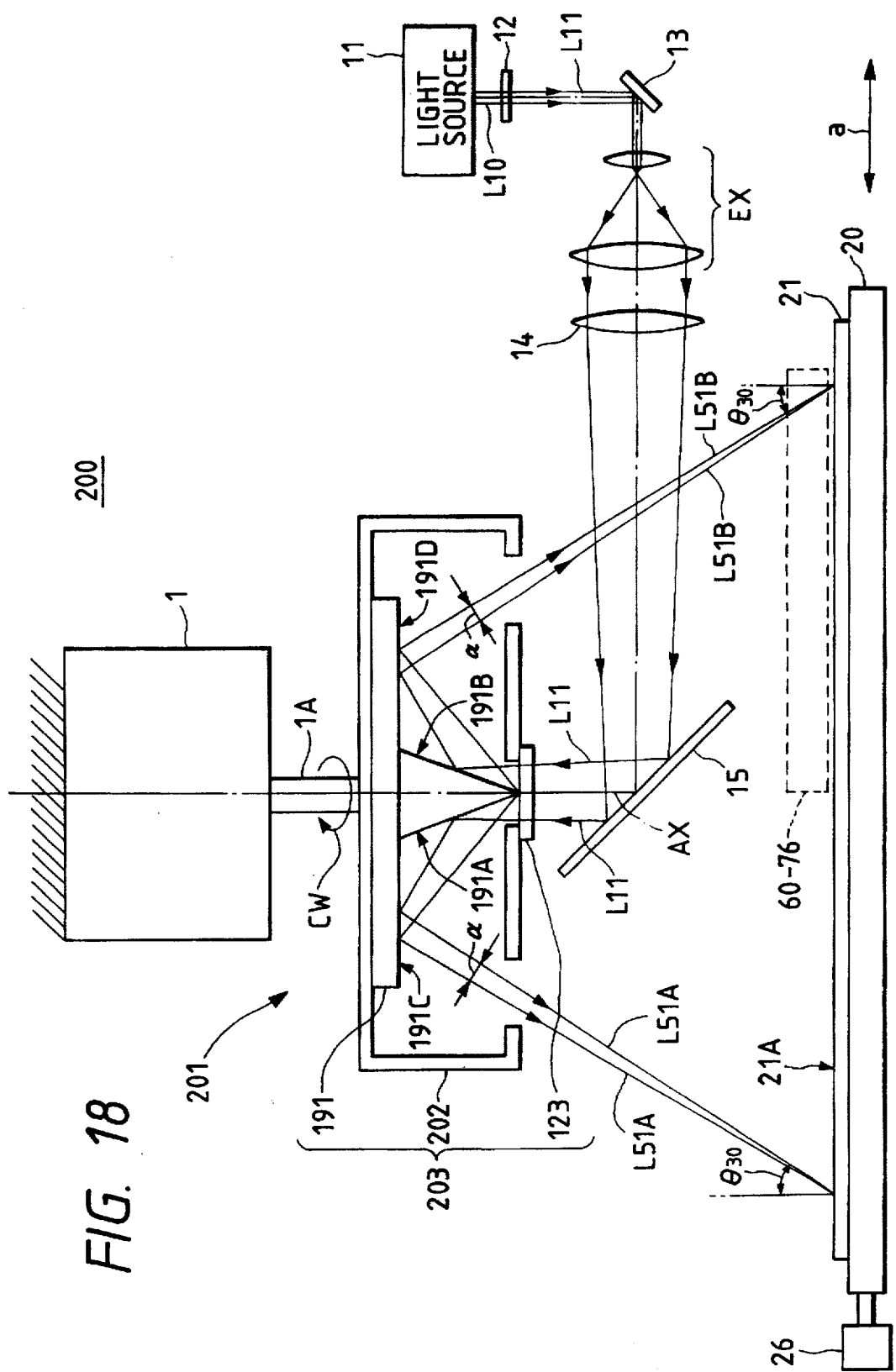
FIG. 18 is a side view showing the overall arrangement of a foreign matter inspection apparatus according to the fourth embodiment of the present invention.

(4-2) Arrangement of Foreign Matter Inspection Apparatus According to Fourth Embodiment A foreign matter inspection apparatus to which the optical scanning device 190 is applied will be explained below. In a foreign matter inspection apparatus 200 shown in FIG. 18 in which the same reference numerals denote corresponding portions as in FIG. 14, an optical scanning device 201 is arranged, so that an optical unit 203 constituted by the rotary mirror 191, a housing 202, and the quarter-wave plate 123 rotates together with the drive shaft 1A of the motor 1, unlike in the optical scanning device 190.

In the optical unit 203, the rotary mirror 191 is fixed to the upper inner surface of the housing 202, and the quarter-wave plate 123 is fixed to the lower outer surface of the housing 202 to cover a window formed coaxially with the drive shaft 1A.

In this foreign matter inspection apparatus 200, a light beam L10 emitted by a laser beam source 11 and consisting of linearly polarized light waves is phase-modulated into circularly polarized light waves via a quarter-wave plate 12, and the modulated light beam is reflected by a reflection mirror 13 to be incident on a beam expander lens system EX. After the light beam is expanded by the beam expander lens system EX, the light beam enters the optical unit 203 via a reflection mirror 15 fixed inside the apparatus as an incident light beam L11 focused at a predetermined aperture angle $\alpha$ via a lens 14.

An incident light beam L11 entering the optical unit 203 is phase-modulated by the quarter-wave plate 123 into linearly polarized light waves, the direction of vibration of an electric vector of which is perpendicular to a plane z-AX$_3$ or z-AX$_4$ including the optical axis AX and the third or fourth reflection surface 191C or 191D.

Thereafter, the light beam is reflected by the third and fourth reflection surfaces 191C and 191D of the rotary mirror 191, and reflected light beams are incident, as first and second reflected light beams L51A and L51B consisting of s-polarized light waves, on a surface 21A to be inspected of a substrate 21 to be inspected placed on a stage 20 via windows formed on the lower surface of the housing 202. At this time, the first and second reflected light beams L51A and L51B scan the surface 21A to be inspected of the substrate 21 to be inspected in an arcuated pattern upon rotation of the optical unit 203 driven by the motor 1, as in the second embodiment described above.

The stage 20 on which the substrate 21 to be inspected is placed is moved in a direction indicated by an arrow a by an actuator 26 which is driven in synchronism with the motor 1, every time the optical unit 203 rotates 180°. With this movement, the first and second reflected light beams L51A and L51B can scan the entire surface 21A to be inspected of the substrate 21 to be inspected.

As in the second embodiment described above, a plurality of light-receiving units 60 to 76, which comprise focusing lenses and light-receiving elements and are the same as those used in the second embodiment, are juxtaposed in an arcuated pattern at equal intervals to obliquely look into the optical scanning line, so as to receive scattered light generated on the surface 21A to be inspected from different space directions when the first and second reflected light beams L51A and L51B scan the surface 21A to be inspected of the substrate 21 to be inspected. Furthermore, as in the second embodiment, a signal processing unit and a main control unit (neither are shown) for processing the light-receiving results of these light-receiving units are arranged. Note that the light-receiving units, signal processing unit, and main control unit applied to the third embodiment are the same as

19

(4-3) Operation of Fourth Embodiment

In the above arrangement, in this foreign matter inspection apparatus 200, a light beam L10 emitted by the laser beam source 11 and consisting of linearly polarized light waves is phase-modulated into circularly polarized light waves by the quarter-wave plate 12, and thereafter, the modulated light beam enters the optical unit 203 of the optical scanning device 201 via the optical system constituted by the reflection mirror 13, the beam expander lens system EX, the lens 14, and the reflection mirror 15, so that the drive shaft 1A of the motor 1 agrees with the optical axis AX.

This incident light beam L11 is converted by the quarter-wave plate 122 of the optical unit 203 into a light beam consisting of linearly polarized light waves, and the converted light beam is reflected by the third and fourth reflection surfaces 191C and 191D of the rotary mirror 191 toward the surface 21A to be inspected of the substrate 21 to be inspected. At the same time, the optical unit 203 is rotated by driving the motor 1. In this manner, first and second reflected light beams L51A and L51B scan the surface 21A to be inspected of the substrate 21 to be inspected.

Furthermore, scattered light generated on the surface 21A to be inspected of the substrate 21 to be inspected at that time is received by the light-receiving units 60 to 76 having a plurality of light-receiving elements as in the second embodiment, and a signal processing unit 80 detects the presence/absence of foreign matter on the basis of the outputs from these light-receiving units 60 to 76.

In this foreign matter inspection apparatus 200, as described above, the incident light beam L11 to be output from the optical scanning device 201 is phase-modulated into linearly polarized light waves, the direction of vibration of the electric vector of which is perpendicular to the plane z-AX$_3$ or z-AX$_4$ including the optical axis AX and the third or fourth reflection surfaces 191C or 191D, and hence, the first and second reflected light beams L51A and L51B are always incident as s-polarized light waves on the surface 21A to be inspected of the substrate 21 to be inspected irrespective of the rotation angle of the optical unit 203 of the optical scanning device 201.

Therefore, this foreign matter inspection apparatus 200 can inspect foreign matter with higher precision than the conventional foreign matter inspection apparatus that does not consider any polarization state of a light beam to be incident on the surface 21A to be inspected of the substrate 21 to be inspected.

Since the rotary mirror 191 is constituted by the first and second reflection surfaces 191A and 191B that do not form right angles therebetween, and the third and fourth reflection surfaces 191C and 191D that form an identical plane, when the drive shaft 1A of the motor 1 causes a static or dynamic axial run-out, the angles formed by the first and second reflected light beams L51A and L51B with respect to the optical axis AX are determined by the angle formed between the first and second reflection surfaces 191A and 191B, and hence, these angles always exhibit a constant value irrespective of the degree of deviation of the drive shaft 1A with respect to the optical axis AX. As a result, even when the drive shaft 1A of the motor 1 causes a static or dynamic axial run-out with respect to the optical axis AX, the first and second reflected light beams L51A and L51B can be optically scanned without being influenced by surface run-outs of the first to fourth reflection surfaces 191A to 191D.

20

(4-4) Effect of Fourth Embodiment

With the above-mentioned arrangement, an incident light beam L11 consisting of circularly polarized light waves is converted by the quarter-wave plate 123 into first and second reflected light beams L51A and L51B having a predetermined polarization state, i.e., consisting of linearly polarized light waves, and the first and second reflected light beams L51A and L51B are deflected by the rotary mirror 111 to be incident on the surface 21A to be inspected of the substrate 21 to be inspected. Also, the first and second reflected light beams L51A and L51B scan the surface 21A to be inspected of the substrate 21 to be inspected by rotating the quarter-wave plate 123 and the rotary mirror 191 by the motor 1 about the optical axis AX of the incident light beam L11 as the rotation shaft 1A. Hence, the apparatus can cope with a large-scale substrate 21 to be inspected, and can detect foreign matter with high precision.

Furthermore, since the rotary mirror 191 is constituted by four plane mirrors serving as the first and second reflection surfaces 191A and 191B that do not form right angles therebetween, and the third and fourth reflection surfaces 191C and 191D that form an identical plane, even when the drive shaft 1A of the motor 1 causes a static or dynamic axial run-out, the first and second reflected light beams L51A and L51B are determined by the angles formed between the first and second reflection surfaces 191A and 191B, thus realizing a foreign matter inspection apparatus that can optically scan the first and second reflected light beams L51A and L51B without being influenced by surface run-outs of the first to fourth reflection surfaces 191A to 191D.

(5) Another Embodiment

In the first to fourth embodiments described above, the optical scanning devices 6, 44, 121, and 201 according to the present invention are respectively applied to the foreign matter inspection apparatuses 10, 50, 120, and 200. However, the present invention is not limited to this, but may be applied to various other apparatuses which are required to cause a light beam having a predetermined polarization state to be incident on a surface to be irradiated of an object to be irradiated (or a surface to be inspected of an object to be inspected).

In each of the first to fourth embodiments described above, the reflection mirror 4, 42, 111, or 191 is applied as the light deflection means for deflecting the light beam L11, which is emitted by the laser beam source 11 and enters the optical scanning device 6, 44, 121, or 201, to be incident on the surface 21A to be inspected of the substrate 21 to be inspected. However, the present invention is not limited to this. For example, a diffraction grating may be used in place of the reflection mirror, and various other deflection means may be used as long as they can deflect the light beam L11 to be incident on the surface 21A to be inspected of the substrate 21 to be inspected.

Furthermore, in the first embodiment described above, a circularly polarized light beam L11 entering the optical scanning device 6 is converted by the quarter-wave plate 3 into a light beam L12, the direction of vibration of the electric vector of which is perpendicular to the z-n plane, thereby adjusting a light beam L13 to be incident on the surface 21A to be inspected of the substrate 21 to be inspected to have a predetermined polarization state with respect to the surface 21A to be inspected. Also, in the second embodiment, a circularly polarized light beam L11 entering the optical scanning device 44 is converted by the quarter-wave plate 41 into a light beam L31, the direction of vibration of the electric vector of which is perpendicular to the z-n$_1$ plane (and z-n$_2$ plane), thereby adjusting first and second light beams L31A and L31B to be incident on the surface 21A to be inspected of the substrate 21 to be inspected to have a predetermined polarization state with respect to the surface 21A to be inspected. However, the present invention is not limited to this, and various other polarization state adjusting means may be adopted as long as they can adjust the polarization state of the light beam L11 so that the light beam L13 or the light beams L31A and L31B to be incident on the surface 21A to be inspected of the substrate 21 to be inspected always have a predetermined polarization state with respect to the surface 21A to be inspected.

Furthermore, in each of the first to fourth embodiments described above, the motor 1 and the housing 2, 40, 122, or 202 are used as rotary driving means for the reflection mirror 4, 42, 111, or 191 and the quarter-wave plate 3, 41, or 123 together, so that a light beam L13, light beams L31A and L31B, light beams L41A and L41B, or light beams L51A and L51B exiting the optical scanning device 6, 44, 121, or 201 can scan the surface 21A to be inspected of the substrate 21 to be inspected. However, the present invention is not limited to this, and various other rotary driving means may be used.

In the first embodiment described above, the light beam L13 is obliquely incident on the surface 21A to be inspected of the substrate 21 to be inspected. However, the present invention is not limited to this. For example, the substrate 21 to be inspected may be disposed, so that the light beam L13 is substantially perpendicularly incident on the surface 21A to be inspected of the substrate 21 to be inspected.

In each of the second to fourth embodiments described above, the 17 light-receiving units 60 to 76 are arranged around the stage 20. However, the present invention is not limited to this. A predetermined number (other than 17) of light-receiving units may be arranged. In this case, the predetermined number of light-receiving units are juxtaposed to receive first and second reflected light beams L31A and L31B, L41A and L41B, or L51A and L51B that form a scanning line 51 corresponding to the 180° revolution of the optical unit 43, 124, or 203 on the surface 21A to be inspected of the substrate 21 to be inspected.

In each of the third and fourth embodiments, the rotary mirror 111 or 191 has a shape symmetrical about a plane having the optical axis AX as the center. However, the present invention is not limited to this, and the rotary mirror need not have such symmetrical shape. That is, various other rotary mirrors may be used as long as they can wavefront-split the first and second reflected light beams L41A and L41B or L51A and L51B to form first and second angles with respect to the optical axis AX, can deflect the first and second reflected light beams L41A and L41B or L51A and L51B in the rotation direction of the rotation axis 1A with reference to the central position of wavefront-splitting so as to cause them to be incident on the surface 21A to be inspected of the substrate 21 to be inspected, and can compensate for a surface run-out error caused by a change in one or both of the first and second angles on the basis of the relative angular deviation between the rotation axis 1A and the optical axis AX so as to maintain the first and second angles to be a constant value.

Furthermore, in each of the third and fourth embodiments, the quarter-wave plate 123 is used as the polarization state adjusting means. However, the present invention is not limited to this. Alternatively, various other means may be used as long as they can adjust the polarization state of the incident light beam L11 so that the incident light beam L11 deflected by the rotary mirror 111 or 191 has a predetermined polarization state with respect to the surface 21A to be inspected of the substrate 21 to be inspected.

Therefore, it is intended that the invention not be limited to the preferred embodiments described herein, but that the invention will include all embodiments falling within the scope of the appended claims.

What is claimed is:

1. An optical scanning device comprising:

light deflection means for deflecting a light beam emitted by a light source to be incident on an object to be irradiated;

polarization state adjusting means for adjusting a polarization state of the light beam, so that the light beam to be incident on the object to be irradiated has a predetermined polarization state with respect to the object to be irradiated; and rotary driving means for rotating said light deflection means and said polarization state adjusting means together so that the light beam deflected by said light deflection means scans the object to be irradiated.

2. A device according to claim 1, wherein said polarization state adjusting means comprises a wave plate, an optic axis of which is tilted through a predetermined angle corresponding to the polarization state of the light beam with respect to a straight line parallel to a plane of incidence of said light deflection means on which the light beam is incident, and perpendicular to a rotation axis of said polarization state adjusting means in a plane including the straight line and perpendicular to the rotation axis.

3. A device according to claim 1, wherein said light deflection means comprises an optical member for splitting the incident light beam into at least two light beams in a rotation direction of said rotary driving means.

4. A foreign matter inspection apparatus for inspecting a presence/absence of foreign matter attached to a surface to be inspected of an object to be inspected, comprising:

a light source for emitting a light beam;

light deflection means for deflecting the light beam emitted by said light source to be incident on the surface to be inspected of the object to be inspected;

polarization state adjusting means for adjusting a polarization state of the light beam, so that the light beam to be incident on the surface to be inspected of the object to be inspected has a predetermined polarization state with respect to the surface to be inspected of the object to be inspected;

rotary driving means for rotating said light deflection means and said polarization state adjusting means together so that the light beam deflected by said light deflection means scans the surface to be inspected of the object to be inspected;

light-receiving means for receiving scattered light of the light beam generated by the foreign matter attached to the surface to be inspected of the object to be inspected, and outputting an electrical signal corresponding to an intensity of the received scattered light; and signal processing means for detecting the foreign matter on the basis of the electrical signal supplied from said light-receiving means.

5. An apparatus according to claim 4, wherein said light deflection means deflects the light beam, so that the light beam scans the surface to be inspected of the object to be inspected in an arcuated pattern, and said light-receiving means comprises a plurality of light-receiving elements which are disposed in an arcuated pattern along a scan position of the light beam on the surface to be inspected of the object to be inspected.

6. An optical scanning device comprising:

rotary driving means having a rotation axis; and light deflection means for wavefront-splitting an incident light beam incident along a first optical axis parallel to the rotation axis into a first light beam that forms a first angle with respect to the first optical axis and a second light beam that forms a second angle with respect to the first optical axis, deflecting the first and second light beams in a rotation direction of the rotation axis with reference to a central position of the wavefront-splitting to cause the first and second light beams to be incident on an object to be irradiated, and compensating for a surface run-out error caused by a change in one or both the first and second angles on the basis of a relative angular deviation between the rotation axis and the first optical axis so as to maintain the first and second angles to be a constant value, wherein said rotary driving means integrally rotates said light deflection means about the rotation axis, so that the first and second light beams wavefront-split and deflected by said light deflection means scan the object to be irradiated.

7. A device according to claim 6, wherein said light deflection means comprises two plane mirrors, i.e., a first plane mirror which forms the first angle with respect to the first optical axis, and a second plane mirror which forms the second angle with respect to the first optical axis, and the first and second angles are equal angles.

8. A device according to claim 6, wherein said light deflection means is constituted by a combination of three plane mirrors, i.e., a first plane mirror which forms the first angle with respect to the first optical axis, a second plane mirror which forms the second angles with respect to the first optical axis, and a third plane mirror having a reflection surface perpendicular to the rotation axis, and the first angle is determined by a reflection angle of the first light beam by said first and third plane mirrors, and the second angle is determined by a reflection angle of the first light beam by said second and third plane mirrors.

9. A device according to claim 6, further comprising polarization state adjusting means for adjusting a polarization state of the incident light beam so that the incident light beam deflected by said light deflection means has a predetermined deflection state with respect to the object to be irradiated, and wherein said rotary driving means rotates said light deflection means and said polarization state adjusting means together about the rotation axis, so that the first and second light beams wavefront-split and deflected by said light deflection means scan the object to be irradiated.

10. A device according to claim 9, wherein said polarization state adjusting means comprises a wave plate, an optic axis of which is tilted, in the plane of incidence of said light deflection means, at a predetermined angle corresponding to the polarization state of the incident light beam with respect to a straight line parallel to a plane of incidence of said light deflection means on which the incident light beam is incident, and perpendicular to a rotation axis of said polarization state adjusting means.

11. A foreign matter inspection apparatus for inspecting a presence/absence of foreign matter attached to a surface to be inspected of an object to be inspected, comprising:

a light source for emitting a light beam;

rotary driving means having a rotation axis;

light deflection means, arranged on an optical path, of the light beam, for wavefront-splitting an incident light beam incident along a first optical axis parallel to the rotation axis into a first light beam that forms a first angle with respect to the first optical axis and a second light beam that forms a second angle with respect to the first optical axis, deflecting the first and second light beams in a rotation direction of the rotation axis with reference to a central position of the wavefront-splitting to cause the first and second light beams to be incident on a surface to be inspected of the object to be inspected, and compensating for a surface run-out error caused by a change in one or both the first and second angles on the basis of a relative angular deviation between the rotation axis and the first optical axis so as to maintain the first and second angles to be a constant value;

light-receiving means for receiving scattered light of the first and second light beams generated by the foreign matter attached to the surface to be inspected of the object to be inspected, and outputting an electrical signal corresponding to an intensity of the received scattered light; and signal processing means for detecting the foreign matter on the basis of the electrical signal supplied from said light-receiving means, wherein said rotary driving means integrally rotates said light deflection means about the rotation axis, so that the first and second light beams wavefront-split and deflected by said light deflection means scan the surface to be inspected of the object to be inspected.

12. An apparatus according to claim 11, wherein said light deflection means comprises two plane mirrors, i.e., a first plane mirror which forms the first angle with respect to the first optical axis, and a second plane mirror which forms the second angle with respect to the first optical axis, and the first and second angles are equal angles.

13. An apparatus according to claim 11, wherein said light deflection means is constituted by a combination of three plane mirrors, i.e., a first plane mirror which forms the first angle with respect to the first optical axis, a second plane mirror which forms the second angles with respect to the first optical axis, and a third plane mirror having a reflection surface perpendicular to the rotation axis, and the first angle is determined by a reflection angle of the first light beam by said first and third plane mirrors, and the second angle is determined by a reflection angle of the first light beam by said second and third plane mirrors.

14. An apparatus according to claim 11, further comprising polarization state adjusting means for adjusting a polarization state of the incident light beam so that the incident light beam deflected by said light deflection means has a predetermined deflection state with respect to the object to be irradiated, and wherein said rotary driving means rotates said light deflection means and said polarization state adjusting means together about the rotation axis, so that the first and second light beams wavefront-split and deflected by said light deflection means scan the object to be irradiated.

15. An apparatus according to claim 14, wherein said polarization state adjusting means comprises a wave plate, an optic axis of which is tilted, in the plane of incidence of said light deflection means, at a predetermined angle corresponding to the polarization state of the incident light beam with respect to a straight line parallel to a plane of incidence of said light deflection means on which the incident light beam is incident, and perpendicular to a rotation axis of said polarization state adjusting means.

* * * * *